United States Patent
Mensonides-Harsema et al.

(10) Patent No.: US 10,703,723 B2
(45) Date of Patent: Jul. 7, 2020

(54) PRODRUGS OF SULFASALAZINE, PHARMACEUTICAL COMPOSITIONS THEREOF AND THEIR USE IN THE TREATMENT OF AUTOIMMUNE DISEASE

(71) Applicant: Truly Translational Sweden AB, Lund (SE)

(72) Inventors: Marguérite Mascha Mensonides-Harsema, Houston, TX (US); Charlott Brunmark, Flyinge (SE); Karin von Wachenfeldt, Lund (SE)

(73) Assignee: TRULY TRANSLATIONAL SWEDEN AB (SE)

( * ) Notice: Subject to any disclaimer, the term of this patent is extended or adjusted under 35 U.S.C. 154(b) by 0 days.

(21) Appl. No.: 16/491,317

(22) PCT Filed: Mar. 8, 2018

(86) PCT No.: PCT/EP2018/055720
§ 371 (c)(1),
(2) Date: Sep. 5, 2019

(87) PCT Pub. No.: WO2018/162625
PCT Pub. Date: Sep. 13, 2018

(65) Prior Publication Data
US 2020/0017446 A1  Jan. 16, 2020

(30) Foreign Application Priority Data
Mar. 9, 2017  (SE) .................................... 1750262

(51) Int. Cl.
*C07D 213/76* (2006.01)
(52) U.S. Cl.
CPC .................................. *C07D 213/76* (2013.01)
(58) Field of Classification Search
CPC .................................................. C07D 213/76
See application file for complete search history.

(56) References Cited

U.S. PATENT DOCUMENTS

| | | | |
|---|---|---|---|
| 2,396,145 A | 3/1946 | Emil et al. | |
| 2010/0048651 A1 | 2/2010 | Gangakhedkar et al. | |

FOREIGN PATENT DOCUMENTS

| CA | 295167 A1 | 12/2015 |
|---|---|---|
| EP | 2418200 A1 | 2/2012 |
| WO | 8801615 A1 | 3/1988 |
| WO | 9732856 A1 | 2/1997 |
| WO | 9722596 A1 | 6/1997 |
| WO | 9730035 A1 | 8/1997 |
| WO | 9813354 A1 | 4/1998 |
| WO | 9902166 A1 | 1/1999 |
| WO | 2000001389 A1 | 1/2000 |
| WO | 0040529 A1 | 7/2000 |
| WO | 0041669 A2 | 7/2000 |
| WO | 2011044239 A2 | 6/2001 |
| WO | 0192224 A1 | 12/2001 |
| WO | 0204434 A1 | 1/2002 |
| WO | 0208213 A1 | 1/2002 |

OTHER PUBLICATIONS

International Search Report dated May 9, 2018 in International Patent Application No. PCT/EP2018/055720.
Fischer et al., "Is Plasma Level Monitoring of Sulfasalazine Indicated in the Treatment of Crohn's Disease or Ulcerative Colitis?" Therapeutic Drug Monitoring, 1980, vol. 2, issue 2, pp. 153-158.
Pullar et al., "Effect of acetylator phenotype on efficacy and toxicity of sulphasalazine in rheumatoid arthritis," Annals of Rheumatic Diseases, 1985, vol. 44, pp. 831-837.
Schröder et al., "Acetylator phenotype and adverse effects of sulphasalazine in healthy subjects," Gut, 1972, vol. 13, pp. 278-284.
Hou et al., "Arylamine N-acetyltransferase polymorphisms in Han Chinese patients with ankylosing spondylitis and their correlation to the adverse drug reactions to sulfasalasine," BMC Pharmacology & Toxicology, 2014, vol. 15, issue 64.

(Continued)

*Primary Examiner* — Joseph R Kosack
(74) *Attorney, Agent, or Firm* — Kim IP Law Group PLLC

(57) ABSTRACT

The present invention relates to new compounds of formula I

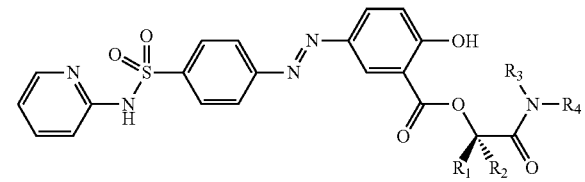

and pharmaceutically acceptable salts and/or co-crystals thereof. The present invention also relates to pharmaceutical compositions comprising these compounds and to their use as medicaments for the prevention, prophylaxis of progression, and/or treatment of a disease in which modulation of extracellular (chemotactic) cytokines and/or TNF-alpha and or nuclear factor kappa B (NFKB) and/or inflammatory cells is beneficial, such as autoimmune diseases, like rheumatoid arthritis, oligoarthritis, spondyloarthropathy, psoriatic arthritis, psoriasis and inflammatory bowel diseases, such as Crohns' disease and ulcerative colitis.

20 Claims, No Drawings

(56) References Cited

OTHER PUBLICATIONS

Jarowicki et al., "Protecting groups," J. Chem. Soc., Perkin Trans. 1, 2001, issue 18, pp. 2109-2135.

Written Opinion dated May 9, 2018 in International Patent Application No. PCT/EP2018/055720.

Rains et al., "Sulfasalazine: A Review of its Pharmacological Properties and Therapeutic Efficacy in the Treatment of Rheumatoid Arthritis," Drugs, 1995, vol. 50, issue 1, pp. 137-156.

Beaulieu et al., "A prodrug strategy for the oral delivery of a poorly soluble HCV NS5B thumb pocket 1 polymerase inhibitor using self-emulsifying drug delivery systems (SEDDS)", Bioorganic & Medical Chemistry Letters, Jan. 2015, vol. 25, issue 2, pp. 210-215; Scheme 1.

Tornhamre et al., "Effects of sulfasalazine and a sulfasalazine analogue on the formation of lipoxygenase and cyclooxygenase products," European Journal of Pharmacology, Oct. 1989, vol. 169, pp. 225-234.

PRODRUGS OF SULFASALAZINE, PHARMACEUTICAL COMPOSITIONS THEREOF AND THEIR USE IN THE TREATMENT OF AUTOIMMUNE DISEASE

CROSS-REFERENCE TO RELATED APPLICATIONS

This application is a U.S. national phase application under 35 U.S.C. § 371 of International Application No. PCT/EP2018/055720 filed on Mar. 8, 2018, which claims priority to Swedish Patent Application No. 1750262-6, filed Mar. 9, 2019, the entire disclosure of each of the applications are hereby incorporated by reference in their entirey for all purposes.

FIELD OF THE INVENTION

The present invention relates to new compounds and pro-drugs of sulfasalazine and pharmaceutically acceptable salts and/or co-crystals thereof. The present invention also relates to pharmaceutical compositions comprising these compounds and to their use as medicaments for the prevention, prophylaxis of progression, and/or treatment of a disease in which modulation of extracellular (chemotactic) cytokines and/or TNF-alpha and or nuclear factor kappa B (NFKB) and/or inflammatory cells is beneficial, such as autoimmune diseases, like rheumatoid arthritis, oligoarthritis, spondyloarthropathy, psoriatic arthritis, psoriasis and inflammatory bowel diseases, such as Crohns' disease and ulcerative colitis.

BACKGROUND OF THE INVENTION

Sulfasalazine (SSZ; salicylazosulfapyridine, salazopyrin, salazopyridine), 2-hydroxy-5-[2-[4-[(2-pyridinylamino)sulfonyl]phenyl]diazenyl]-benzoic acid, was first described in U.S. Pat. No. 2,396,145. Sulfasalazine forms brownish-yellow crystals. It has 4 theoretical $pK_a/_b$ values, which are at 0.6, 2.4, 9.7 and 11.8, a water solubility of less than 0.05 mg/mL at ambient temperature and a melting point of 240 to 245° C. Sulfasalazine decomposes at a temperature of 260 to 265° C. The structure of sulfasalazine is shown below:

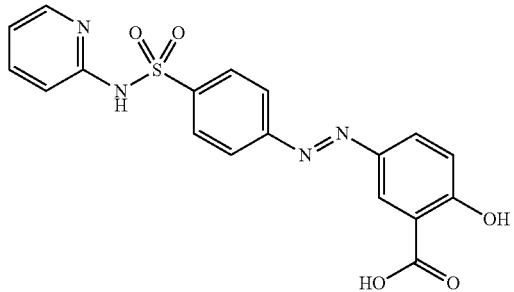 [SMILES: O=C(O)c1cc(/N=N/c2ccc(S(=O)(=O)Nc3ccccn3)cc2)ccc1O]

Sulfasalazine is known to be highly effective in the prevention, prophylaxis of progression, and/or treatment of several different autoimmune diseases, for example rheumatoid arthritis, juvenile idiopathic arthritis, ankylosing spondylitis, and ulcerative colitis. It is one of the most widely used small molecule disease-modifying antirheumatic drugs (DMARDs), either as stand-alone therapy or in combination with glucocorticoids and/or in combination with other small molecule DMARDs, such as methotrexate and/or hydroxychloroquine and/or biological DMARDs, such as anti TNF-alpha biologics (for example infliximab, golimumab and adalimumab).

Neither the mode nor site of action of sulfasalazine in autoimmune diseases, in which it has been found to be therapeutically effective, has been elicited with certainty. In addition, these diseases are of unknown aetiology. It is generally assumed that the therapeutic effect of sulfasalazine stems from its metabolite sulfapyridine (SP). However, it is to date unknown whether the ability of sulfasalazine to successfully treat autoimmune diseases stems from sulfasalazine itself, or partially to completely from its metabolites. Both non-clinical and clinical studies so far have failed to provide conclusive evidence in either direction.

In adults, guided by tolerability and efficacy, sulfasalazine is typically administered orally at dose levels of 500 to 6000 mg per day. Tablets contain 500 mg of the active pharmaceutical ingredient. Commercially available tablets include both immediate and modified release compositions, which are taken one to three times daily, typically about one hour prior to a meal to avoid food effects. The systemic bioavailability of sulfasalazine in man is low, only 15 to 20° of an oral dose is absorbed in the small intestine. Upon multiple dosing, steady state levels of sulfasalazine are reached within 24 hours.

The intra- and inter-variability of systemic levels of sulfasalazine and its major metabolites at a given dose level is high. For example, mean serum levels following oral administration of 4000 mg/day typically are between 10 and 15 ug/mL, with a $C_{max}$ at 4 to 12 h.

Sulfasalazine is subject to entero-hepatic clearance. Both non-absorbed and enterohepatically cleared sulfasalazine is transformed by aza-reducing gut flora to 5-aminosalicylic acid (which has a systemic bioavailability from 10 to 30°) and sulfapyridine (which has a systemic bioavailability of about 60°). Following the oral administration of sulfasalazine, these metabolites can be detected in the plasma after about 10 hours. In the liver, non-enterohepatically cleared sulfasalazine is also metabolized to 5-aminosalicylic acid and sulfapyridine, the latter one being associated with the common side effects like nausea, headache, dry mouth, vomiting and diarrhoea (Schroeder and Evans, Gut, 1972, 13, 278-284) seen in SSZ therapy.

The major hepatic metabolite of sulfapyridine is the acetylated form, which is formed through arylamine N-acetyltransferase 2 (NAT2). The rate of acetylation is genetically determined and follows a bimodal distribution. In 60° of the general population, the acetylation rate is slow, while in the remaining 40° of the general population, the acetylation rate is fast. Steady state levels of sulfapyridine and its acetyl-metabolite are reached after 72 h, with typical mean serum levels of 17 to 45 ug/mL for sulfapyridine and 8 to 21 ug/mL (25 to 62° of SP) of acetylated sulfapyridine (slow and fast acetylators, respectively). In slow acetylators, the steady state levels are reached sooner, which is accompanied by a faster onset of adverse events like nausea and vomiting (Schroeder and Evans, Gut, 1972, 13, 278-284). There is no difference in absorption characteristics, plasma protein binding (ca. 50°) or apparent distribution volume (0.9 L/kg) between fast and slow acetylators. However, the elimination half-life of sulfapyridine in slow acetylators (15.3 h) is almost three times longer than the elimination half-life in fast acetylators (5.5 h), and the total plasma clearance in fast acetylators (135.3 mL/min) is almost four times faster than in slow acetylators (36.9 mL/min) (Fischer and Klotz, Ther. Drug Monit. 1980, 2, 153).

In a retrospective study in rheumatoid arthritis (3 g/day for 24 weeks) similar efficacy rates of sulfasalazine were found, regardless of the acetylator phenotype. In a prospective study in rheumatic arthritis (RA) (24 weeks), fast acetylators treated with 3 g/day sulfasalazine showed a marked improvement in the overall clinical status, while the overall clinical status of slow acetylators, that were being treated with half of the SSZ dose, remained unchanged. However, the drop-out rates, due to nausea and vomiting, at the low treatment dose of 1.5 g/d, were three times greater in the slow acetylator group (Pullar et al, Ann. Rheum. Dis. 1985, 44, 831-837). In a prospective study in ankylosing spondylitis (AS) in Han Chinese patients, the prevalence and time of onset of SSZ-induced AEs were related to the polymorphic type of NAT1 and NAT2. The incidence of both overall and dose-related adverse events (AEs) were significantly higher in the NAT2 slow acetylator phenotype. The prevalence of drug termination in NAT2 slow acetylator patients was significantly higher than in fast acetylator patients. (Hou et al, BMC Pharmacol. Toxicol. 2014, 15, 64).

This is consistent with findings in studies in healthy volunteers, where in the different acetylator phenotype higher steady state levels of sulfapyridine correlate with the time of onset, the rate of occurrence and the perceived severity of side effects. In RA patients with a slow acetylation rate, the ratio found for the blood plasma steady state concentration ($C_{SS}$) and the infinite area under the curve of plasma concentrations ($AUC_{0\to\infty}$) of SP vs SSZ, when treated with 2 g/d of sulfasalazine, is 6 and 5.5, respectively (Rains et al, Drugs 1995, 50, 137-156). In a healthy volunteer study with a population of 63° slow acetylators, the ratio found for the $AUC_{0\to\infty}$ of SP vs SSZ was 4.

Sulfasalazine is a substrate for the ABCG2 transporter protein, which is highly expressed at the apical membrane of both enterocytes in the gut lumen and hepatocytes in the liver. These tissues that are typically involved in both absorption and bioavailability (F) and/or disposition and/or biliary excretion (hepatic clearance) of drugs. The ABCG2 gene is subject to polymorphism, where the nucleotide changes from c.421C/C to C/A results in a reduced efflux activity. The incidence of this polymorphism is estimated to be between 7-11° in Caucasians, 26-35° in East Asians and less than 1° in Sub-Saharan Africans. Yamasaki et al (2008) demonstrated in healthy Japanese volunteers that, following oral administration of sulfasalazine, both ABCG2 and NAT2 gene polymorphisms play an important role in the pharmacokinetics of sulfasalazine, sulfapyridine and its acetylated metabolite Ac-sulfapyridine. The mean $AUC_{0-48}$ and $C_{max}$ of sulfasalazine were significantly higher, and the mean $CL_{total}/F$ was significantly lower in subjects with at least one ABCG2-A mutant allele, which was independent of the NAT2 genotype. The pharmacokinetic values of sulfapyridine and its acetylated metabolite appeared to be dependent on both the NAT2 genotype and the ABCG2 genotype, however. Since total urinary and biliary recovery of sulfasalazine have been reported to be very low in humans, as supported by non-clinical data in portal-vein-cannulated rats (Matsuda et al. 2013), the contribution of the ABCG2 transporter protein to the biliary excretion of sulfasalazine is believed to be small.

The high affinity of sulfasalazine for the ABCG2 transporter and/or its poor water solubility are believed to contribute to the low systemic bioavailability of this drug. Therefore, relatively high oral dose levels of sulfasalazine are needed to reach sufficient systemic levels for it to be efficacious in the prevention, prophylaxis of progression, and/or treatment of autoimmune diseases, like rheumatoid arthritis. High oral dose levels and low systemic bioavailability of sulfasalazine drive the high systemic levels of its metabolite sulfapyridine (which causes its inherent side effects), as the unabsorbed sulfasalazine is converted to sulfapyridine in the lower intestinal tract and subsequently absorbed into the blood stream.

The high affinity of sulfasalazine for the ABCG2 transporter is of special importance in a setting of systemic inflammation, as is prevalent in the targeted diseases like rheumatoid arthritis. It is well known, that the pharmacokinetic profile of small molecules, like the currently marketed DMARDs, can be dramatically changed during the inflammation stage in autoimmune disease, which is due to altered expression levels of metabolizing enzymes and/or transporter proteins. This results in altered plasma levels and/or the volume of distribution of the parent compound and/or its metabolites, as compared to a non-inflammation situation prevalent in the general population and possibly in patients in remission. Polymorphisms in metabolizing enzymes and/or transporter proteins and/or co-administration of modulators of such metabolizing enzymes and/or transporter proteins also affect the pharmacokinetics of sulfasalazine and co-administered DMARDs in such patients, as compared to general patient populations. In consequence, the benefit/risk profile in a disease stage of significant inflammation may be different from the benefit/risk profile found during non- or low-inflammation stage and/or to the benefit/risk profile found in patients with polymorphisms in metabolizing enzymes and/or transporter proteins. Dosing and managing over-dosing and side effects are thus challenging when administering SSZ.

WO88/01615 discloses ester derivatives of carboxylic acid medicaments. These new derivatives provide the characteristic pharmacological response and are less irritating to mucosa than the acids from which they are derived, while the cleaved off moiety is of a non-toxic nature to humans. The bioavailability from the site of administration is faster in these esters compared to the original carboxylic acid medicaments. The exemplified medicaments are acute treatment medicaments, such as pain killers, for which faster absorption rates are highly preferred. However, the disclosure does not deal with the problem of increased absorption for medicaments that need to be administered repeatedly over a longer time period (chronic disease treatment) in diseases that, for example, are of an autoinflammatory nature, where the pharmacokinetics, i.e. absorption, maximum concentration in the blood stream ($C_{max}$) and area under the curve (AUC), are known to differ during the acute disease flare as compared to disease remission, and for which the total amount of drug in the body from a given dose regimen, e.g. the AUC at steady state, needs to be increased in order to enhance the pharmacodynamic exposure to the carboxylic acid from which it is derived.

EP2418200 discloses new NSAID's phtalimide derivatives that aim to potentiate the anti-inflammatory and analgesic activity by acting synergistically on two fronts, i.e. by inhibiting the cyclooxygenase (COX) and inhibiting TNF-alpha. Preferably, esters and amides are obtained that are not usable in pharmaceutical compositions as prodrugs. A process is disclosed, wherein the phtalimide derivatives are obtained from prodrugs. It is unclear whether the compounds are to be understood as prodrugs of parent compounds or are parent compounds themselves. Two alkyl ester sulfasalazine-phatalimide derivatives, where X is —$CH_2$—O— or —$CH_2CH_2$—O— are shown as compounds 58 and 59. It is well-known, that N-phtamimidoalkyl esters are chemically unstable at low pH and can be readily hydrolyzed in acidic conditions, such as the stomach. Other examples include a sulfasalazine-phtalimide derivative, where X is —NH— (compound 57), as well as sulfasalazine-phtalimide derivatives, where X is either a benzyl-O— or benzyl-alkyl-O— (compounds 60-63).

Sulfasalazine is not classified as an NSAID (non-steroidal anti-inflammatory drug) but is classified as a DMARD (disease modifying anti rheumatic drug). Further, sulfasalazine is itself an inhibitor of TNF-alpha. Therefore, a hybridization strategy to create a phtalimide derivative is neither needed nor logical. Besides, gastro-ulceration related to the carboxylic acid moiety of sulfasalazine can be overcome with the use of excipients that prevent the pharmaceutical composition from releasing sulfasalazine prior to reaching the intestinal tract. Such modified release forms of solid oral pharmaceutical compositions containing sulfasalazine are available on the market.

Pro-drugs of methyl hydrogen fumarate are used to treat multiple sclerosis and psoriasis. The intention of these pro-drugs is to reduce the lack of tolerance of fumarate treatments that stem from the wide spread and/or serious gastro-intestinal side effects that are believed to be caused by the carboxylic acid group of fumarates. In a broad range of known fumarate derivatives, US2010048651 discloses a new set of fumarate derivatives. A list of the chemical and enzymatic stability of a small selection of the compounds is disclosed. The compounds are tested under a limited range of conditions. However, the stability studies do not include the chemical stability at the relevant pH ranges that are found in the upper gastro-intestinal tract (pH 1-7.4) nor the stability in human-derived in vitro systems. The selected examples in US2010048651 do not clearly show that glycolamide derivatives of fumarates in general show a differentiated chemical or enzymatic stability as compared to other, structurally close derivatives of fumarates, especially not at pH 1-7.4 nor in human blood plasma. In addition, it is unclear how the absolute oral bioavailability of the disclosed compounds is different from dimethylfumarate itself (referred to in US2010048651 as 2), as results are being compared to a compound IV, which appears not to be disclosed in the patent application.

CA2951627 discloses prodrugs of naphthofuranes, specifically of Napabucasin (2-Acetyl-4H,9H-naphtho[2,3-b]furan-4,9-dione), which is described as compound (A). In compounds of general formula (IA) and (I), the $CH_3$ group of the acetyl moiety of Napabucasin is derivatized with an ester function that carries substituent $R^2$. $R^2$ is an alkyl group that can by optionally substituted further with halogens, heteroatoms (N, O, S) and cyclic groups, and includes glycolamides (compounds 72 and 73). Following oral administration or incubation in plasma or liver microsomes, the 1-($R^2$)-3-oxo-3-naphthofuran-proprionates that are disclosed are positioned at the C2 position and converted to Napabucasin. This document shows that an acetyl function of a compound, when converted to a 3-oxo-1-($C_{1-6}$alkyl)-propionate, independent of the substitution pattern of the $C_{1-6}$alkyl group, is metabolized by the body to the acetyl group, even when the $C_{1-6}$alkyl contains a glycolamide (compounds 72 and 73). The formation of an acetyl group from a pro-drug instead of a carboxyl acid is not of interest as a pro-drug for sulfasalazine.

Beaulieu, et al, Bioorg Med Chem Lett, 2015, January, Vol 25, No 2, pp 210-215, discloses a wide range of ionizable and non-ionizable $C_{1-4}$alkyl esters of the parent compound 2, in which the alkyl moiety is optionally substituted with halogen (Cl, P) or heteroatoms (N, O) or cyclic substituents, including glycolic amide substituents. The parent compound has a limited lipid solubility. The lipid solubility is improved in several ester analogues of the parent compound, including some, but not all, glycolic amide ester analogues. Most glycolic amide esters are readily converted to the parent compound 2 in liver microsomes. It is also stated that the pro-drugs reduce the efflux of protein transporters.

Sulfasalazine is absorbed in the small intestine. All non-absorbed sulfasalazine is consequently metabolized in the colon by bacteria into sulfapyridine which is absorbed into the blood. Because sulfapyridine causes side effects, it is preferred that substantially all sulfasalazine is absorbed in the small intestine and not metabolized in the colon. If more of the applied oral dose of sulfasalazine or a derivative thereof is absorbed in the small intestine, an overall lower oral dose of sulfasalazine (or derivative) can be administered, leading to a lower systemic exposure levels of sulfapyridine, less side effects and thus a more favourable sulfasalazine vs sulfapyridine plasma ratio.

For this to be achieved, the solubility of sulfasalazine needs to be increased without affecting the efflux by the protein transporters, such that sulfasalazine or its derivative can be absorbed in the small intestine without being metabolized in the colon into the side-effect-causing sulfapyridine. This problem is not addressed in the prior art documents mentioned above.

Thus, there is still a need for compounds and/or pharmaceutical compositions containing such compounds, that exhibit the therapeutic efficacy of sulfasalazine itself in the prevention, prophylaxis of progression, and/or treatment of autoimmune diseases, like rheumatoid arthritis or ankylosing spondylitis, with improved gastrointestinal permeability and/or absorption with an ordered enzymatic hydrolysis, i.e. minimal cleavage in the gut lumen prior to absorption.

There is still a need for improved aqueous solubility, improved oral availability and increased plasma levels of sulfasalazine with/without altered plasma levels ratios of sulfasalazine/sulfapyridine and its metabolites. There is a need for improved efficacy/responder rate, improved overall tolerability and/or increased safety, such as reduced gastro-intestinal and/or renal toxicity. Preferably the inter- and intra-variability in pharmacokinetics in the inflammatory stage and/or remission stage of autoimmune diseases, like rheumatoid arthritis, can be decreased as well as reducing the effect of co-administration with food. There is a need for reduced dosing frequency, decreased susceptibility to polymorphisms in transporter proteins and/or metabolizing enzymes. This will most likely improve compliance to drug treatment schedules and improved treatments in autoimmune diseases, like small molecule and/or biologic DMARDs and/or glucocorticosteroids. Costs for health care would thus be reduced.

SUMMARY OF THE INVENTION

The present invention is directed to a compound of formula I, a pharmaceutically acceptable salt, crystals and/or co-crystal thereof, diastereomer, enantiomer, or mixture thereof, wherein:

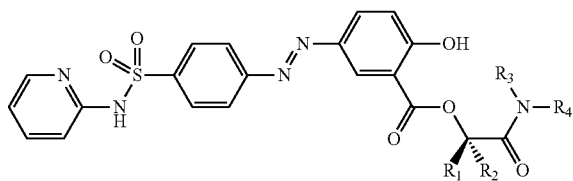

I $R^1$ and $R^2$ are independently chosen from the group comprising or consisting of hydrogen and $C_{1-6}$alkyl, $R^3$ and $R^4$ are independently chosen from the group comprising or consisting of hydrogen, $C_{1-6}$alkyl, $C_{1-6}$heteroalkyl, $C_{3-12}$cycloalkyl, $C_{3-12}$heterocycloalkyl, $C_{5-13}$aryl, $C_{5-13}$heteroaryl, $C_{3-12}$cycloalkyl$C_{1-6}$alkyl, $C_{3-12}$heterocycloalkyl$C_{1-6}$alkyl, $C_{5-13}$aryl$C_{1-6}$alkyl and $C_{5-13}$heteroaryl$C_{1-6}$alkyl, or $R^3$ and $R^4$ together with the nitrogen to which they are attached form a ring chosen from $C_{3-12}$heterocycloalkyl and $C_{5-13}$heteroaryl, and wherein $R^1$, $R^2$, $R^3$ and $R^4$ are optionally substituted with one or more R, R is independently chosen from the group comprising or consisting of halogen, —OH, —SH, —CN, —CF$_3$, ═O, —NO$_2$, —C(O)NR$^5$R$^6$, —R$^5$, —OR$^5$, —SR$^5$, —C(O)R$^5$, —COOR$^5$ and —NR$^5$R$^6$, wherein $R^5$ and $R^6$ are independently chosen from the group comprising or consisting of hydrogen, $C_{1-4}$alkyl and $C_{1-4}$cycloalkyl, and optionally substituted with one or more $R^7$, wherein $R^7$ is chosen from the group comprising or consisting of halogen, —OH, —SH, —CN, —CF$_3$, ═O, —NO$_2$, —C(O)NR$^8$R$^9$, —R$^8$, —OR$^8$, —SR$^8$, —C(O)R$^8$, —COOR$^8$ and —NR$^8$R$^9$, wherein $R^8$ and $R^9$ are independently chosen from the group comprising or consisting of hydrogen, $C_{1-4}$alkyl and $C_{1-4}$cycloalkyl.

The novel compounds, as compared to sulfasalazine, display a high gastrointestinal permeability and/or absorption. The compounds have an improved aqueous solubility, e.g. a 10- to 100-fold increased solubility compared to sulfasalazine. The novel compounds further display an ordered enzymatic hydrolysis, i.e. minimal pH- and/or temperature-dependent chemical cleavage in the gut lumen prior to absorption. The efflux of sulfasalazine is not affected by the pro-drugs. The glycol amide ester as prodrugs of sulfasalazine are converted by the body to a carboxylic acid in an ordered enzymatic hydrolysis, which improves gastrointestinal permeability and/or absorption.

The compounds of the invention are believed to change the ratio of the kinetic parameters like $C_{max}$ and AUC and thus the systemic exposure of sulfasalazine vs sulfapyridine in favour of sulfasalazine. If more of the sulfasalazine can be absorbed in the upper parts of the intestine, less sulfasalazine is left to be metabolized to sulfapyridine in the colon. As a result, side effects caused by sulfapyridine following the metabolization of the azide bond in sulfasalazine by the bacteria that are present in the colon, are reduced. This is especially relevant for metabolizers of the slow NAT2 type, as sulfapyridine remains longer in their blood stream due to slow acetylation of sulfapyridine.

The compounds of the invention are stable for at least 60 minutes in human whole blood and plasma. The compounds of the invention are chemically stable in aqueous liquids at pH ranging from 1 to 8.

It is believed that the compounds of the invention, as compared to presently available pharmaceutical compositions of sulfasalazine, have an increased efficacy/responder rate; facilitate the use of lower dosing strengths per dosing and/or a reduced dosing frequency per day and/or standardized dosing regimens. It is believed that the compounds of the invention, as compared to presently available pharmaceutical compositions of sulfasalazine, have reduced food effects; reduced gastrointestinal side effects/toxicity and/or nausea. It is believed that the compounds of the invention, as compared to presently available pharmaceutical compositions of sulfasalazine, have a reduced interpatient treatment variability.

One embodiment relates to the compound of formula I, wherein $R^1$ and $R^2$ are $C_{1-4}$alkyl, and $R^3$ and $R^4$ are independently chosen from the group comprising or consisting of hydrogen, $C_{1-6}$alkyl, $C_{1-6}$heteroalkyl, $C_{3-12}$cycloalkyl, $C_{3-12}$heterocycloalkyl, $C_{5-13}$aryl, $C_{5-13}$heteroaryl, $C_{3-12}$cycloalkyl$C_{1-6}$alkyl, $C_{3-12}$heterocycloalkyl$C_{1-6}$alkyl, $C_{5-13}$aryl$C_{1-6}$alkyl and $C_{5-13}$heteroaryl$C_{1-6}$alkyl, or $R^3$ and $R^4$ together with the nitrogen to which they are attached form a ring chosen from $C_{3-12}$heterocycloalkyl and $C_{5-13}$heteroaryl, and wherein $R^1$, $R^2$, $R^3$ and $R^4$ are optionally substituted with one or more R, wherein R is independently chosen from the group comprising or consisting of halogen, —OH, —SH, —CN, —CF$_3$, ═O, —NO$_2$, —C(O)NR$^5$R$^6$, —R$^5$, —OR$^5$, —SR$^5$, —C(O)R$^5$, —COOR$^5$ and —NR$^5$R$^6$, wherein $R^5$ and $R^6$ are independently chosen from the group comprising or consisting of hydrogen, $C_{1-4}$alkyl and $C_{1-4}$cycloalkyl, and optionally substituted with one or more $R^7$, wherein $R^7$ is chosen from the group comprising or consisting of halogen, —OH, —SH, —CN, —CF$_3$, ═O, —NO$_2$, —C(O)NR$^8$R$^9$, —R$^8$, —OR$^8$, —SR$^8$, —C(O)R$^8$, —COOR$^8$ and —NR$^8$R$^9$, wherein $R^8$ and $R^9$ are independently chosen from the group comprising or consisting of hydrogen, $C_{1-4}$alkyl and $C_{1-4}$cycloalkyl.

Another embodiment relates to the compound of formula I, wherein $R^1$ is hydrogen and $R^2$ is $C_{1-4}$ alkyl, $R^3$ and $R^4$ are independently chosen from the group comprising or consisting of hydrogen, $C_{1-6}$alkyl, $C_{1-6}$heteroalkyl, $C_{3-12}$cycloalkyl, $C_{3-12}$heterocycloalkyl, $C_{5-13}$aryl, $C_{5-13}$heteroaryl, $C_{3-12}$cycloalkyl$C_{1-6}$alkyl, $C_{3-12}$heterocycloalkyl$C_{1-6}$alkyl, $C_{5-13}$aryl$C_{1-6}$alkyl and $C_{5-13}$heteroaryl$C_{1-6}$alkyl, or $R^3$ and $R^4$ together with the nitrogen to which they are attached form a ring chosen from the group comprising or consisting of $C_{3-12}$heterocycloalkyl and $C_{5-13}$heteroaryl, and wherein $R^1$, $R^2$, $R^3$ and $R^4$ are optionally substituted with one or more R, wherein R is independently chosen from the group comprising or consisting of halogen, —OH, —SH, —CN, —CF$_3$, ═O, —NO$_2$, —C(O)NR$^5$R$^6$, —R$^5$, —OR$^5$, —SR$^5$, —C(O)R$^5$, —COOR$^5$ and —NR$^5$R$^6$, wherein $R^5$ and $R^6$ are independently chosen from the group comprising or consisting of hydrogen, $C_{1-4}$alkyl and $C_{1-4}$cycloalkyl, and optionally substituted with one or more $R^7$, wherein $R^7$ is chosen from the group comprising or consisting of halogen, —OH, —SH, —CN, —CF$_3$, ═O, —NO$_2$, —C(O)NR$^8$R$^9$, —R$^8$, —OR$^8$, —SR$^8$, —C(O)R$^8$, —COOR$^8$ and —NR$^8$R$^9$, wherein $R^8$ and $R^9$ are independently chosen from the group comprising or consisting of hydrogen, $C_{1-4}$alkyl and $C_{1-4}$cycloalkyl.

A further embodiment relates to the compound of formula I, wherein $R^1$ is hydrogen and $R^2$ is chosen from methyl, ethyl, or isopropyl, $R^3$ and $R^4$ are independently chosen from the group comprising or consisting of hydrogen, $C_{1-6}$alkyl, $C_{1-6}$heteroalkyl, $C_{3-12}$cycloalkyl, $C_{3-12}$heterocycloalkyl, $C_{5-13}$aryl, $C_{5-13}$heteroaryl, $C_{3-12}$cycloalkyl$C_{1-6}$alkyl, $C_{3-12}$heterocycloalkyl$C_{1-6}$alkyl, $C_{5-13}$aryl$C_{1-6}$alkyl and $C_{5-13}$heteroaryl$C_{1-6}$alkyl, or $R^3$ and $R^4$ together with the nitrogen to which they are attached form a ring chosen from $C_{3-12}$heterocycloalkyl and $C_{5-13}$heteroaryl, and wherein $R^1$, $R^2$, $R^3$ and $R^4$ are optionally substituted with one or more R, wherein R is independently chosen from the group comprising or consisting of halogen, —OH, —SH, —CN, —$CF_3$, =O, —$NO_2$, —C(O)$NR^5R^6$, —$R^5$, —$OR^5$, —$SR^5$, —C(O)$R^5$, —$COOR^5$ and —$NR^5R^6$, wherein $R^5$ and $R^6$ are independently chosen from the group comprising or consisting of hydrogen, $C_{1-4}$alkyl and $C_{1-4}$cycloalkyl, and optionally substituted with one or more $R^7$, wherein $R^7$ is chosen from the group comprising or consisting of halogen, —OH, —SH, —CN, —$CF_3$, =O, —$NO_2$, —C(O)$NR^8R^9$, —$R^8$, —$OR^8$, —$SR^8$, —C(O)$R^8$, —$COOR^8$ and —$NR^8R^9$, wherein $R^8$ and $R^9$ are independently chosen the group comprising or consisting of from hydrogen, $C_{1-4}$alkyl and $C_{1-4}$cycloalkyl.

Another embodiment relates to the compound of formula I, wherein $R^1$ and $R^2$ are hydrogen, $R^3$ and $R^4$ are independently chosen from the group comprising or consisting of hydrogen, $C_{1-4}$alkyl, $C_{1-4}$heteroalkyl, $C_{3-7}$cycloalkyl, $C_{3-7}$heterocycloalkyl, $C_{5-6}$aryl, $C_{5-6}$heteroraryl, $C_{3-6}$cycloalkyl$C_{1-4}$alkyl, $C_{3-6}$heterocycloalkyl$C_{1-4}$alkyl, $C_{5-6}$aryl$C_{1-4}$alkyl and $C_{5-6}$heteroaryl$C_{1-4}$alkyl, or $R^3$ and $R^4$ together with the nitrogen to which they are attached form a ring chosen from $C_{3-8}$heterocycloalkyl and $C_{5-6}$heteroaryl, and wherein $R^1$, $R^2$, $R^3$ and $R^4$ are optionally substituted with one or more R. R is independently chosen from the group comprising or consisting of halogen, —OH, —SH, —CN, —$CF_3$, =O, —$NO_2$, —C(O)$NR^5R^6$, —$R^5$, —$OR^5$, —$SR^5$, —C(O)$R^5$, —$COOR^5$ and —$NR^5R^6$, wherein $R^5$ and $R^6$ are independently chosen the group comprising or consisting of from hydrogen, $C_{1-4}$alkyl and $C_{1-4}$cycloalkyl, and optionally substituted with one or more $R^7$, wherein $R^7$ is chosen from the group comprising or consisting of halogen, —OH, —SH, —CN, —$CF_3$, =O, —$NO_2$, —C(O)$NR^8R^9$, —$R^8$, —$OR^8$, —$SR^8$, —C(O)$R^8$, —$COOR^8$ and —$NR^8R^9$, wherein $R^8$ and $R^9$ are independently chosen from the group comprising or consisting of hydrogen, $C_{1-4}$alkyl and $C_{1-4}$cycloalkyl.

Another embodiment relates to the compound of formula I, wherein $R^1$ and $R^2$ are hydrogen, $R^3$ and $R^4$ are independently chosen from the group comprising or consisting of hydrogen, $C_{1-6}$alkyl, $C_{3-12}$cycloalkyl, $C_{3-12}$cycloalkyl$C_{1-6}$alkyl, or $R^3$ and $R^4$ together with the nitrogen to which they are attached form a ring chosen from $C_{3-12}$heterocycloalkyl; and wherein $R^3$ and $R^4$ are optionally substituted with one or more R, and R is —$OR^5$ or $R^5$ wherein $R^5$ is $C_{1-4}$alkyl.

One embodiment relates to the compound of formula I, wherein $R^1$ and $R^2$ are hydrogen, $R^3$ and $R^4$ are independently chosen from hydrogen, $C_{1-4}$alkyl, $C_{3-6}$cycloalkyl, $C_{3-6}$cycloalkyl$C_{1-4}$alkyl, or $R^3$ and $R^4$ together with the nitrogen to which they are attached form a ring chosen from $C_{3-7}$heterocycloalkyl; and wherein $R^3$ and $R^4$ are optionally substituted with one or more R, and R is —$OR^5$ or $R^5$ wherein $R^5$ is $C_{1-4}$alkyl. In one embodiment, $R^5$ is methyl or methoxy.

A further embodiment relates to the compound of formula I, wherein $R^1$ and $R^2$ are hydrogen, $R^3$ and $R^4$ are independently chosen from the group comprising or consisting of methyl, ethyl, propyl, butyl, pentyl, hexyl, methoxy, cyanomethyl, methoxymethyl, hydroxymethyl, 2-oxoethyl, 2-aminoethyl, 2-hydroxyethyl, 2-cyanoethyl, 1-methylethyl, 2-methylethyl, 1,1-dimethylethyl, 2-methoxyethyl, 1-methoxyethyl, 2-hydroxy-1-methylethyl, 2-cyano-1-methylethyl, 2,2-difluoroethyl, 2,2,2-trifluoroethyl, 2-(dimethylamino)ethyl, 2-amino-2-ethoxyethyl, 1-methylpropyl, 2-methylpropyl, 3-aminopropyl, 2-hydroxypropyl, 3-hydroxypropyl, 1,1-dimethylpropyl, 2,2-dimethylpropyl, 2-methoxypropyl, 2-cyanopropyl, 3-methoxypropyl, 2-hydroxy-2-methylpropyl, 2,3-dihydroxypropyl, 3-(ethenyloxy)propyl, 3-oxobutyl, 1-methylbutyl, 2-methylbutyl, 3-methylbutyl, 1,1-dimethylbutyl, 4-hydroxybutyl, 2-propyn-1-yl, 2-propen-1-yl, 1-methyl-2-propyn-1-yl, 2-methyl-2-propen-1-yl, 3-buten-1-yl, 2-amino-1-methylethyl, 1-cyclopenten-1-yl, cyclopropyl, 1-(hydroxymethyl)cyclopropyl, cyclobutyl, 3-hydroxy-cyclobutyl, 3-methoxy-cyclobutyl, 1-cyanocyclobutyl, cyclopentyl, 1-methylcyclopentyl, 3-methylcyclopentyl, 2-hydroxycyclopentyl, 3-hydroxycyclopentyl, 2,3-dihydroxycyclopentyl, cyclohexyl, 1H-pyrrol-2-yl, 1H-pyrrol-3-yl, 3-pyrrolidinyl, tetrahydro-3-furanyl, 3-pyridinyl, 2-thienyl, 1H-pyrrol-2-ylmethyl, 1H-pyrrol-3-ylmethyl, 2-furanylmethyl, 1-H-imidazol-2-yl, 1-methyl-1-H-pyrazol-3-yl, 5-methyl-2-furanyl, 1-cyclohexen-1-yl, 1-cyclopenten-1-yl, 4-methyl-4H-1,2,4-triazol-3-yl, 1H-1,2,4-triazol-5-ylmethyl, 2-thiazolyl, 4-piperidinyl, 1-methyl-3-pyrrolidinyl, 1,3,4-thiadiazol-2-yl, phenyl, cyclopropylmethyl, cyclobutylmethyl, cyclopentylmethyl, (1-hydroxycyclobutyl)methyl, (1-hydroxycyclobutyl)methyl, (3-hydroxycyclobutyl)methyl, (3-methoxycyclobutyl)-methyl, (tetrahydro-2-furanyl)methyl, (tetra hydro-3-furanyl)methyl, 2-cyclopropylethyl, 1-cyclobutylethyl, and 2-cyclobutylethyl.

One embodiment relates to the compound of formula I, wherein $R^1$ and $R^2$ are hydrogen and $R^3$ and $R^4$ together with the nitrogen to which they are attached form a ring chosen from $C_{3-7}$heterocycloalkyl, optionally substituted with methyl.

A further embodiment relates to the compound of formula I, wherein $R^1$ and $R^2$ are hydrogen, and wherein $R^3$ and $R^4$ together with the nitrogen to which they are bonded/attached form are selected from the group comprising or consisting of ethenone: azetidinyl, 3-methyl-azetidinyl, 3-amino-azetidinyl, 3-hydroxy-azetidinyl, 3-fluoro-azetidinyl, 3-cyclopropyl-azetidinyl, 2,4-dimethyl-azetidinyl, 3,3-dimethyl-azetidinyl, 3-hydroxy-3-methyl-azetidinyl, 3-fluoro-3-methyl-azetidinyl, 3-cyano-3-methyl-azetidinyl, 3-aminomethyl-azetidinyl, 3-dimethylminomethyl-azetidinyl, 3-hydroxymethyl-azetidinyl, 2-(1-methylethyl)-azetidinyl, pyrrolidinyl, 3-methyl-pyrrolidinyl, 3-hydroxy-pyrrolidinyl, 3,4-dimethyl-1-pyrrolidinyl, 2,3-dimethyl-1-pyrrolidinyl, 2-amino-pyrrosidinyl, 3-amino-pyrrolidinyl, 2-isoxazolidinyl, 2-pyrrolidinone, piperidinyl, 4-methyl-1-piperidinyl, 2-methyl-1-piperidinyl, 2-imidazolidinone, tetrahydro-2H-pyridazinyl, piperazinyl, oxazolidinone, 4-morpholinyl, tetrahydro-2H-1,2-oxazin-2-yl, 2-cyano-pyrrolidinyl, 3-aminomethyl-pyrrolidinyl, 3-methylamino-pyrrolidinyl, 3-amino-piperidinyl, 2-azabicyclo(2,2,1)hept-2-yl, 2,5-diazabicyclo(2,2,1)hept-2-yl, 2-piperidinone, 4-piperidinone, 2-oxa-5azabicyclo(2,2,1)hept-5-yl, hexahydro-1H-azepin-1-yl, hexahydro-1H-1,4-diazepam-1-yl, 2-methyl-piperazinyl, 2-methylamino-pyrrolidinyl, 3-methylamino-pyrrolidinyl, 3-methyl-piperazinyl, 4-hydroxy-piperadinyl, 3-hydroxy-piperadinyl, 2-methyl-4-morpholinyl, 3-methyl-4-morpholinyl, 3-hydroxymethyl-pyrrolidinyl, 2-hydroxymethyl-pyrrolidinyl, 3-hydroxymethyl-pyrrolidinyl, 3-hydroxy-4-methyl-pyrrolidinyl, tetra hydro-1,2-oxazapin-2-(3H)-yl, 3-(2-hydroxyethyl)-azetidinyl, 4-hydroxy-2-methyl-pyrrolidinyl, 3-hydroxy-3-methyl-pyrrolidinyl, 3-methoxy-3-methyl-azetidinyl, 3,4-dihydroxy-pyrrolidinyl, 4-thiomorpholinyl, 3,3-difluoro-pyrrolidinyl, 4-cyano-1,2,3,6-tetrahydro-pyridinyl, 4-ethynyl-piperadinyl, 3-ethynyl-3-hydroxy-pyrrolidinyl, 2-azobicyclo(2,2,2)oct-2-yl, hexahydrocyclopenta[c]pyrrol-2(1H)-yl, 5-azaspiro[2,5]oct-5-yl, 5-azaspiro[3,4]oct-2-yl, 2-azasprior[3,4]oct-2-yl, 5-azaspiro[3,4]oct-6-yl, hexahydrocyclopenta[b]pyrrol-1 (2H)-yl, 3-cyanoethyl-3-hydroxy-azetidinyl, 2-cyano-morpholinyl, 3-cyano-morpholinyl, hexahydropyrrolo-[3,4-c]pyrrol-2(1H)-yl, hexahydro-2H-azepin-2-one, 1H-pyrrol-1- yl, 3,6-dihydro-2H-pyridinyl, 2-ethyl-1H-pyrrol-1-yl, 3,6-dihydro-5-methyl-1(2H)-pyridinyl, 5-methyl-3(2H)-isoxazolone, 3,6-dihydro-4,5-dimethyl-1(2H)-pyridinyl and 3,6-dihydro-3,5-dimethyl-1(2H)-pyridinyl.

A further embodiment relates to the compound of formula I, wherein $R^1$ and $R^2$ are hydrogen and $R^3$ and $R^4$ together with the nitrogen to which they are attached form a 3-methyl-azetidine, azetidine, pyrrolidine, piperidine, piperazine, morpholine or azepane.

One embodiment relates to the compound of formula I, wherein $R^1$, $R^2$ and $R^3$ are hydrogen and $R^4$ is selected from the group comprising or consisting of methyl, ethyl, propyl, butyl, pentyl, hexyl, methoxy, cyanomethyl, methoxymethyl, hydroxymethyl, 2-oxoethyl, 2-aminoethyl, 2-hydroxyethyl, 2-cyanoethyl, 1-methylethyl, 2-methylethyl, 1,1-dimethylethyl, 2-methoxyethyl, 1-methoxyethyl, 2-hydroxy-1-methylethyl, 2-cyano-1-methylethyl, 2,2-difluoroethyl, 2,2,2-trifluoroethyl, 2-(dimethylamino)ethyl, 2-amino-2-ethoxyethyl, 1-methylpropyl, 2-methylpropyl, 3-aminopropyl, 2-hydroxypropyl, 3-hydroxypropyl, 1,1-dimethylpropyl, 2,2-dimethylpropyl, 2-methoxypropyl, 2-cyanopropyl, 3-methoxypropyl, 2-hydroxy-2-methylpropyl, 2,3-dihydroxypropyl, 3-(ethenyloxy)propyl, 3-oxobutyl, 1-methylbutyl, 2-methylbutyl, 3-methylbutyl, 1,1-dimethylbutyl, 4-hydroxybutyl, 2-propyn-1-yl, 2-propen-1-yl, 1-methyl-2-propyn-yl, 2-methyl-2-propen-1-yl, 3-buten-1-yl, 2-amino-1-methylethyl, 1-cyclopenten-1-yl, cyclopropyl, 1-(hydroxymethyl)cyclopropyl, cyclobutyl, 3-hydroxycyclobutyl, 3-methoxy-cyclobutyl, 1-cyanocyclobutyl, cyclopentyl, 1-methylcyclopentyl, 3-methylcyclopentyl, 2-hydroxycyclopentyl, 3-hydroxycyclopentyl, 2,3-dihydroxycyclopentyl, cyclohexyl, 1H-pyrrol-2-yl, 1H-pyrrol-3-yl, 3-pyrrolidinyl, tetrahydro-3-furanyl, 3-pyridinyl, 2-thienyl, 1H-pyrrol-2-ylmethyl, 1H-pyrrol-3-ylmethyl, 2-furanylmethyl, 1-H-imidazol-2-yl, 1-methyl-1-H-pyrazol-3-yl, 5-methyl-2-furanyl, 1-cyclohexen-1-yl, 1-cyclopenten-1-yl, 4-methyl-4H-1,2,4-triazol-3-yl, 1H-1,2,4-triazol-5-yl-methyl, 2-thiazolyl, 4-piperidinyl, 1-methyl-3-pyrrolidinyl, 1,3,4-thiadiazol-2-yl, phenyl, cyclopropylmethyl, cyclobutylmethyl, cyclopentylmethyl, (1-hydroxycyclobutyl)methyl, (1-hydroxycyclobutyl)methyl, (3-hydroxycyclobutyl)methyl, (3-methoxycyclobutyl)-methyl, (tetrahydro-2-furanyl)methyl, (tetrahydro-3-furanyl)methyl, 2-cyclopropylethyl, 1-cyclobutylethyl, and 2-cyclobutylethyl.

Another embodiment relates to the compound of formula I, wherein $R^1$ and $R^2$ are hydrogen and $R^3$ is methyl, ethyl, propyl, isopropyl, butyl, isobutyl, 2-hydroxyethyl, 2-methoxyethyl, cyclopentyl, cyclohexyl or cyclopropylmethyl, and $R^4$ is methyl, ethyl, propyl, isopropyl, butyl, isobutyl, 2-hydroxyethyl, 2-methoxyethyl, cyclopentyl, cyclohexyl or cyclopropylmethyl.

Yet another embodiment relates to the compound of formula I, wherein $R^1$ and $R^2$ are hydrogen and $R^3$ is hydrogen, methyl, ethyl, methylethyl and $R^4$ is methyl, ethyl, propyl, isopropyl, butyl, isobutyl, 2-hydroxyethyl, 2-methoxyethyl, cyclopentyl, cyclohexyl or cyclopropylmethyl.

Yet a further embodiment relates to the compound of formula I, wherein $R^1$ and $R^2$ are hydrogen and $R^3$ is hydrogen, methyl, ethyl, propyl, isopropyl or butyl and $R^4$ is cyclopentyl, cyclohexyl or cyclopropylmethyl.

Another embodiment relates to the compound of formula I, wherein $R^1$ and $R^2$ are hydrogen and $R^3$ is methyl, dimethyl, ethyl and $R^4$ is methyl, ethyl, butyl, methylethyl or cyclohexyl.

The solubility as compared to sulfasalazine as well as the aqueous stability as compared to other known esters of sulfasalazine at pH levels ranging from 1 to 10 and at temperatures ranging from 0 to 45° C. is improved in compounds of formula I, in particular in examples of a compound of formula I in which the substituents on $R^1$, $R^2$, $R^3$ and $R^4$ are relatively short, for example if the substituents are selected from hydrogen, methyl, ethyl, propyl, isopropyl, butyl, isobutyl, methanol, ethanol, methoxy, ethoxy, cyclopropyl, cyclobutyl, cyclopentyl, cyclohexyl, cyclopropylmethyl, piperazinyl, morpholinyl, azidinyl, pyrrolidinyl, piperidinyl or furanyl.

Compounds of formula I, whereby $R^1$ and $R^2$ are hydrogen and $R^3$ and $R^4$ are relatively short, for example substituents selected from hydrogen, methyl, ethyl, propyl, isopropyl, isobutyl, butyl, isobutyl, methanol, ethanol, propanol, methoxy, ethoxy, cyclopropyl, cyclobutyl, cyclopentyl, cyclohexyl, cyclopropylmethyl, piperazinyl, morpholinyl, azidinyl, pyrrolidinyl, piperidinyl and furanyl have improved aqueous solubility and chemical stability properties.

Compounds of formula I, whereby $R^1$, $R^2$ and $R^3$ are hydrogen and $R^4$ is relatively short, for example selected from methyl, ethyl, propyl, isopropyl, isobutyl, butyl, methanol, ethanol, propanol, methoxy, ethoxy, cyclopropyl, cyclobutyl, cyclopentyl, cyclohexyl, cyclopropylmethyl, have improved aqueous solubility and chemical stability properties.

The invention also relates to any one of compound or a pharmaceutically acceptable salt, crystals or co-crystal thereof, selected from the group comprising or consisting of
2-morpholino-2-oxoethyl-2-hydroxy-5-((4-(N-(pyridine-2-yl)sulfamoyl)phenyl)diazenyl)benzoate,
2-(3-methyl-azetidinyl)-2-oxoethyl-2-hydroxy-5-((4-(N-(pyridine-2-yl)sulfamoyl)phenyl)diazenyl)benzoate,
2-azetidinyl-2-oxoethyl-2-hydroxy-5-((4-(N-(pyridine-2-yl)sulfamoyl)phenyl)diazenyl)benzoate,
2-pyrrolidinyl-2-oxoethyl-2-hydroxy-5-((4-(N-(pyridine-2-yl)sulfamoyl)phenyl)diazenyl)benzoate,
2-piperidinyl-2-oxoethyl-2-hydroxy-5-((4-(N-(pyridine-2-yl)sulfamoyl)phenyl)diazenyl)benzoate,
2-piperazinyl-2-oxoethyl-2-hydroxy-5-((4-(N-(pyridine-2-yl)sulfamoyl)phenyl)diazenyl)benzoate, and
2-azepanyl-2-oxoethyl-2-hydroxy-5-((4-(N-(pyridine-2-yl)sulfamoyl)phenyl)diazenyl)benzoate.

The invention also relates to any one of compound or a pharmaceutically acceptable salt, crystals or co-crystal thereof, selected from the group comprising or consisting of
2-(ethylamino)-2-oxoethyl-2-hydroxy-5-((4-(N-(pyridine-2-yl)sulfamoyl)phenyl)diazenyl)benzoate,
2-(isobutylamino)-2-oxoethyl-2-hydroxy-5-((4-(N-(pyridine-2-yl)sulfamoyl)phenyl)diazenyl)benzoate,
2-(cyclopentylamino)-2-oxoethyl-2-hydroxy-5-((4-(N-(pyridine-2-yl)sulfamoyl)phenyl)diazenyl)benzoate,
2-(methylamino)-2-oxoethyl-2-hydroxy-5-((4-(N-(pyridine-2-yl)sulfamoyl)phenyl)diazenyl)benzoate,
2-(isopropylamino)-2-oxoethyl-2-hydroxy-5-((4-(N-(pyridine-2-yl)sulfamoyl)phenyl)diazenyl)benzoate,
2-((cyclopropyl methyl)amino)-2-oxoethyl-2-hydroxy-5-((4-(N-(pyridine-2-yl)sulfamoyl)phenyl)diazenyl)benzoate,
2-(propylamino)-2-oxoethyl-2-hydroxy-5-((4-(N-(pyridine-2-yl)sulfamoyl)phenyl)diazenyl)benzoate,
2-(2-methoxylethyl)amino)-2-oxoethyl-2-hydroxy-5-((4-(N-(pyridine-2-yl)sulfamoyl)phenyl)diazenyl)benzoate,
2-(dimethylamino)-2-oxoethyl-2-hydroxy-5-((4-(N-(pyridine-2-yl)sulfamoyl)phenyl)diazenyl)benzoate, 2-(diethylamino)-2-oxoethyl-2-hydroxy-5-((4-(N-(pyridine-2-yl)sulfamoyl)phenyl)diazenyl)benzoate,
2-(dipropylamino)-2-oxoethyl-2-hydroxy-5-((4-(N-(pyridine-2-yl)sulfamoyl)phenyl)diazenyl)benzoate,
2-(dibutylamino)-2-oxoethyl-2-hydroxy-5-((4-(N-(pyridine-2-yl)sulfamoyl)phenyl)diazenyl)benzoate, and
2-(di-(1-methylethylamino))-2-oxoethyl-2-hydroxy-5-((4-(N-(pyridine-2-yl)sulfamoyl)phenyl)diazenyl)benzoate.

The invention also relates to any one of compound or a pharmaceutically acceptable salt, crystals or co-crystal thereof, selected from the group comprising or consisting of
N-ethyl-N-methylamino-2-oxoethyl-2-hydroxy-5-((4-(N-(pyridine-2-yl)sulfamoyl)phenyl)diazenyl)benzoate,
N-methyl-N-2-methylethylamino-2-oxoethyl-2-hydroxy-5-((4-(N-(pyridine-2-yl)sulfamoyl)phenyl)diazenyl)benzoate,
N-butyl-N-methylamino)-2-oxoethyl-2-hydroxy-5-((4-(N-(pyridine-2-yl)sulfamoyl)phenyl)diazenyl)benzoate,
N-methyl-N-(2,2-dimethylpropyl)amino-2-oxoethyl-2-hydroxy-5-((4-(N-(pyridine-2-yl)sulfamoyl)phenyl)diazenyl)benzoate,
N-butyl-N-ethylamino-2-oxoethyl-2-hydroxy-5-((4-(N-(pyridine-2-yl)sulfamoyl)phenyl)diazenyl)benzoate,
N-cyclohexyl-N-methylamino-2-oxoethyl-2-hydroxy-5-((4-(N-(pyridine-2-yl)sulfamoyl)phenyl)diazenyl)benzoate,
N-ethyl-N-cyclohexylamino-2-oxoethyl-2-hydroxy-5-((4-(N-(pyridine-2-yl)sulfamoyl)phenyl)diazenyl)benzoate, and
N-(2-(methylethyl)-N-(2,2-dimethyl propyl)amino-2-oxoethyl-2-hydroxy-5-((4-(N-(pyridine-2-yl)sulfamoyl)phenyl)diazenyl)benzoate.

These compounds fall within the scope of compounds of formula I. It is to be understood that this list of compounds is included in the wording "compound of formula I, or a pharmaceutically acceptable salt, crystals or co-crystals, hydrates or solvents, diastereomer, enantiomer thereof" or "compound(s) of the invention", as used in embodiments related to uses, pharmaceutical compositions or processes, unless specified otherwise.

The invention also relates to the compound of formula I, as defined above, for use in therapy.

In an embodiment, the invention relates to a compound of formula I, or a pharmaceutically acceptable salt or co-crystal thereof, for use in the prevention, progression, prophylaxis and/or treatment of a disease in which modulation of the inflammatory regulator nuclear factor kappa B (NFKB) and/or (chemotactic) cytokines is beneficial, such as in autoimmune diseases.

In an embodiment, the compound as defined above, are for use in therapy in patients that are of the slow acetylation NAT2 phenotype.

The invention also relates to the compound of formula I, as defined above, for use in the prevention, prophylaxis of progression, and/or treatment of autoimmune diseases, whereby the ratio of pharmacokinetic parameters (e.g. plasma concentrations either after single dose administration or at steady state, for example Cmax and/or AUC) of sulfasalazine to sulfapyridine in blood plasma after oral administration of the compound as defined above, compared to said ratio after oral administration of sulfasalazine, is improved by at least a factor 1.1 to 100, or 1.5 to 50, or 2, or 3, or 5, or 10.

Another embodiment relates to the compound of formula I, as defined above, for use in prevention, progression, prophylaxis and/or treatment of autoimmune diseases.

One embodiment relates to the compound of formula I, as defined above, for use in prevention, progression, prophylaxis and/or treatment of arthritides associated with or including osteoarthritis or osteoarthrosis, both primary and secondary to dysplasia, such as congenital hip dysplasia, cervical and lumbar spondylitis, low back and neck pain, reactive arthritis, undifferentiated spondyloarthropathy, septic arthritis, infection-related arthopathies and bone disorders, such as tuberculosis, Potts' disease and Poncet's syndrome, acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma, mixed connective tissue disease, and undifferentiated connective tissue disease, inflammatory myopathies including dermatomyositis and polymyositis, polymalgia rheumatic, juvenile arthritis including idiopathic inflammatory arthritides of whatever joint distribution and associated syndromes, and rheumatic fever and its systemic complications, vasculitides including giant cell arteritis, Takayasu's arteritis, Churg-Strauss syndrome, polyarteritis nodos, microscopic polyarteritits, and vasculitides associated with viral infection, hypersensitivity reactions, cryoglobulins, and paraproteins, Familial Mediterranean fever, Muckle-Wells syndrome, and Familial Hibernian Fever, Kikuchi disease; drug-induced arthralgias, tendonititides, and myopathies.

An active juvenile form of any of these diseases may exist and any such juvenile form is included in any of the mentioned diseases.

Yet another embodiment relates to the compound of formula I, as defined above, for use in prevention, progression, prophylaxis and/or treatment of rheumatoid arthritis and the active juvenile idiopathic form thereof and Stills' disease.

Another embodiment relates to the compound of formula I, as defined above, for use in prevention, progression, prophylaxis and/or treatment of oligoarthritis, and the active juvenile idiopathic form thereof.

A further embodiment relates to the compound of formula I, as defined above, for use in prevention, progression, prophylaxis and/or treatment of polyarthritis and the active juvenile idiopathic form thereof.

A further embodiment relates to the compound of formula I, as defined above, for use in prevention, progression, prophylaxis and/or treatment of seronegative spondyloarthropathies including ankylosing spondylitis, spondyloarthropathy with peripheral arthritis, axial spondyloarthritis and the active juvenile idiopathic forms thereof.

A further embodiment relates to the compound of formula I, as defined above, for use in prevention, progression, prophylaxis and/or treatment of psoriatic arthritis and the active juvenile idiopathic form thereof.

A further embodiment relates to the compound of formula I, or a pharmaceutically acceptable salt or co-crystal thereof, as defined above, for use in prevention, progression, prophylaxis and/or treatment of plaque psoriasis.

A further embodiment relates to the compound of formula I, as defined above, for use in prevention, progression, prophylaxis and/or treatment of dermatological diseases, including, but not limited to pemphigus vulgaris, pyoderma gangrenosum, dermatitis herpetiformis, alopecia areata, lichen planus, corticosteroid-dependent chronic idiopathic urticaria, plaque psoriasis, cutaneous lupus erythematosus and atrophy blanche.

A further embodiment relates to the compound of formula I, as defined above, for use in prevention, progression, prophylaxis and/or treatment of systemic or cutaneous lupus erythematosus.

A further embodiment relates to the compound of formula I, as defined above, for use in prevention, progression, prophylaxis and/or treatment of inflammatory bowel diseases, including eosinophilic gastro-enteritis, mastocytosis, Crohn's disease, colitis, including ulcerative colitis, proctitis, coeliac disease, irritable bowel syndrome and food-related allergies, which may have effects remote from the gut, such as migraine, rhinitis or eczema.

A further embodiment relates to the compound of formula I, as defined above, for use in prevention, progression, prophylaxis and/or treatment of Crohn's disease and ulcerative colitis including juvenile idiopathic forms thereof.

A further embodiment relates to the compound of formula I, as defined above, for use in prevention, progression, prophylaxis and/or treatment of glioma.

Another embodiment relates to the compound of formula I, as defined above, for use in therapy or in use for any one of the disease, disorder or condition are mentioned above.

The invention relates to a method of treating, preventing, preventing or reducing the risk of a disease in which modulation of the inflammatory regulator nuclear factor kappa B (NFKB) and/or the modulation of expression and/or extra-cellular levels of (chemotactic) cytokines and/or the modulation of a persistent anti-inflammatory cell response is beneficial.

The invention relates to a method of treating, preventing, preventing or reducing the risk of a disease, disorder or condition in which modulation of autoimmune diseases is beneficial, which comprises administering to a mammal, such as a human, in need thereof, a therapeutically effective amount of a compound of formula I, as defined above.

Another embodiment relates to said method of treating, preventing, preventing or reducing the risk of autoimmune diseases.

A further embodiment relates to said method of treating, preventing, preventing or reducing the risk arthritides any one of the disease, disorder or condition are mentioned above.

The invention further relates to a pharmaceutical composition comprising the compound of formula I, as defined above, in the association with a pharmaceutically acceptable adjuvant, diluent or carrier.

The invention also relates to a process for the preparation of a pharmaceutical composition, as defined above, which comprises mixing a compound of formula I, as defined above, with a pharmaceutically acceptable adjuvant, diluent or carrier.

One embodiment relates to a use of the pharmaceutical composition, as defined above, in therapy, or for the prevention, progression, prophylaxis and/or treatment of a disease in which modulation of auto inflammatory processes, such as prevalent in (certain stages of) autoimmune diseases is beneficial. Examples of such disease, disorder or condition are mentioned above.

The invention also relates to the use of a compound of formula I, as defined above, in the manufacture of a medicament for the prevention, progression, prophylaxis and/or treatment of a disease in which modulation of modulation of the inflammatory regulator nuclear factor kappa B (NFKB) and/or of extracellular (chemotactic) cytokines and/or TNF-alpha and/or interleukins and/or CC, CXC, CX3C or CX3CR1 chemokines, and/or inflammatory cells is beneficial. Examples of such diseases are mentioned above.

The prevention, progression, prophylaxis and/or treatment of diseases in which modulation of the inflammatory regulator nuclear factor kappa B (NFKB) and/or of extra-cellular (chemotactic) cytokines, and/or inflammatory cells is beneficial and related pathology defined herein may be applied as a sole therapy or may involve, in addition to the compound of the invention, conjoint treatment with conventional therapy of value in treating one or more disease mentioned above.

Such conjoint prevention, progression, prophylaxis and/or treatment may be achieved by way of the simultaneous, sequential or separate dosing of the individual compounds of the invention or additional agents of the prevention, progression, prophylaxis and/or treatment. Such combination products employ the compounds, or pharmaceutically acceptable salts or co-crystals thereof, of the invention.

In one embodiment, the invention relates to a pharmaceutical composition comprising (i) a compound of formula I, as defined above, (ii) an additional therapeutic agent, or a pharmaceutically acceptable salt thereof, and (iii) one or more pharmaceutically acceptable excipient, carrier or diluent.

In an embodiment, the invention relates to a pharmaceutical composition comprising (i) a compound of formula I, as defined above, together with one or more pharmaceutically acceptable excipient, carrier or diluent (ii) an additional therapeutic agent, or a pharmaceutically acceptable salt thereof, together with one or more pharmaceutically acceptable excipient, carrier or diluent.

In another embodiment, the invention relates to a pharmaceutical composition comprising (i) a compound of formula I, as defined above, (ii) at least one agent selected from the group consisting of methotrexate, hydroxychloroquine and sulfasalazine, or a pharmaceutically acceptable salt thereof, and (iii) one or more pharmaceutically acceptable excipient, carrier or diluent.

In yet another embodiment, the invention relates to a pharmaceutical composition comprising (i) a compound of formula I, as defined above, (ii) at least one agent selected from the group consisting of biologic, like a TNF-alpha inhibitor (for example infliximab, adalimumab, certolizumab, etanercept, golimumab), or IL-6 inhibitor (for example tocilizumab), or B-cell blocker (for example rituximab), or T-cell blocker (for example abatacept), or IL-1 inhibitor (for example anakinra), or IL-17 inhibitor (for example secukinumab, ixekizumab), or IL12/23 inhibitor (for example ustekinumab) and (iii) one or more pharmaceutically acceptable excipient, carrier or diluent.

The invention relates to a process for the preparation of the compounds of formula I as defined above, comprising or consisting of the steps of:
(i) mixing sulfasalazine and 1.0 to 1.5 equivalent of base in an organic solvent under stirring for 0.5 to 4 h at a temperature between 15 and 60° C.,
(ii) adding 1.0 to 1.5 equivalent of halo-acetamide in an organic solvent under stirring for 10 to 48 h at a temperature between 60 to 130° C., optionally in the presence of KI,
(iii) cooling and partition between an aqueous saturated NaCl solution and organic solvent, drying the organic solvent using an anhydrous MgSO4 or Na2SO4 or similar, filtrating and evaporating the solvent, and
(iv) purifying using chromatography and/or crystallization.

One embodiment relates to the process of preparation of a compound of formula I, as defined above using DMF in steps (i) and/or (ii) and ethyl acetate in step (iii). Another embodiment relates to the process of preparation of a compound of formula I, as defined above using a Cl-acetamide as the halo-acetamide. Yet another embodiment relates to the process of preparation of a compound of formula I, as defined above using an I-acetamide as the halo-acetamide. One embodiment relates to the process of preparation of a compound of formula I, as defined above using a mixture of ethyl acetate, triethylamine and methanol in step (iv) to obtain the purified compound of formula I. Where reference is made in this specification to any of the foregoing compounds of formula I, including any specific polymorphic form and/or a pharmaceutically acceptable salt or co-crystal of any of the foregoing compounds of formula I. A specific compound or form will be substantially free of any other physical compounds and/or specific polymorphic forms. I.e. in one embodiment, a specific compound is a least 80° by weight, or at least 85° by weight, or at least 90° by weight, e.g. at least 90, 91, 92, 93, 94, 95, 96, 97, 98, 99 or 100 by weight, substantially pure.

DETAILED DESCRIPTION OF PREFERRED EMBODIMENTS OF THE INVENTION

The definitions set forth in this application are intended to clarify terms used throughout this application. The term "herein" means the entire application.

As used herein, the term "disease" is intended to include disorder, condition or any equivalent thereof.

As used herein, the term "patient" refers to a mammal, for example, a human.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

As used herein, a dash ("—") that is not between two letters of symbols is used to indicate a point of attachment for a moiety of substituent. For example, —CN is a cyano group bonded through the carbon atom of said group.

As used herein, the term "compounds of the invention" refers to the compound of formula I, or or any mixture thereof, or a pharmaceutically acceptable salt or crystals, co-crystal, hydrate or solvate, diastereomer or enantiomer thereof. Certain compounds may exist in multiple crystalline, co-crystalline, or amorphous forms.

As used herein, the term "optional" or "optionally" means that the subsequently described event or circumstance may but need not occur, and that the description includes instances where the event or circumstance occurs and instances where it does not.

As used herein, the terms "$C_n$", used alone or as a suffix or prefix, is intended to include hydrocarbon-containing groups; n is an integer from 1 to 10.

As used herein, the term "halogen" or "halo", used alone or as suffix or prefix, is intended to include bromine, chlorine, fluorine and iodine.

As used herein, the term "hetero", used alone or as a suffix or prefix, is intended to include alkyl, cycloalkyl and aryl groups in which one or more of the carbon atoms (and certain associated hydrogen atoms) are independently replaced with the same or different hetero atoms (S, O or N) or heteroatomic groups. Examples of heteroatomic groups include, but are not limited to, —O—, —S—, —O—O—, —S—S—, —O—S—, NR, =N—N=, —N=N—, —N=N—NR—, —PR—, —P(O)$_2$—, —POR—, —O—P(O)$_2$—, —SO—, —SO$_2$—, —Sn(R)$_2$—, and the like, where each R is independently chosen from hydrogen, (substituted) alkyl, (substituted) aryl, (substituted) arylalkyl, (substituted) cycloalkyl, (substituted) heterocyclic alkyl, (substituted) heteroaryl, or (substituted) heteroarylalkyl. Reference to, for example, a $C_6$heteroalkyl includes groups having five carbon atoms and one heteroatom, groups having four carbon atoms and two heteroatoms, etc. Reference to, for example, a $C_6$heterocycloalkyl includes aliphatic ring systems that have five carbon atoms and one heteroatom, aliphatic ring systems having four carbon atoms and two heteroatoms, etc. In certain embodiments, a heteroatomic group is chosen from —O—, —S—, —NH—, —N(CH$_3$)—, and —SO$_2$—; and in certain embodiments, the heteroatomic group is —O—.

As used herein, the term "alkyl", used alone or as a suffix or prefix, is intended to include both saturated or unsaturated, branched or straight chain, monovalent hydrocarbon radical derived by the removal of one hydrogen atom from a single carbon atom or atom or a parent alkane, alkene or alkyne. Examples include, but are not limited to methyl; ethyls, such as ethanyl, ethenyl, ethynyl; propyls such as propan-1-yl, propan-2-yl, prop-1-en-1-yl, prop-1-en-2-yl, prop-2-en-1-yl, prop-1-yn-1-yl, prop-2-yn-1-yl, etc; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yl-3-yl, but-3-yn-1-yl, etc.; and the like. The term "alkyl" is specifically intended to include groups having any degree or level of saturation, including groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl and alkynyl are used.

As used herein, the term "cycloalkyl", used alone or as a suffix or prefix, is intended to include both saturated or partially unsaturated cyclic alkyl radical. Where a specific level of saturation is intended, the nomenclature cycloakanyl or cycloalkenyl is used. Examples of cycloalkyl groups include, but is not limited to, groups derived from cyclopropane, cyclobutene, cyclopentane, cyclohexane and the like. As used herein, the term "heterocycloalkyl" denotes a cycloalkyl comprising at least one heteroatom selected from O, N or S, such as morpholinyl, azetidinyl, azepane, and the like.

As used herein, the term "aryl" refers to a either a monocyclic aromatic ring having 5 or 6 ring members or a multiple ring system having at least one carbocyclic aromatic ring fused to at least one carbocyclic aromatic ring, cycloalkyl ring or heterocycloalkyl ring. For example, aryl includes a phenyl ring fused to a 5- to 7-membered heterocycloalkyl ring containing one or more heteroatoms independently selected from N, O, and S.

As used herein, the term "heteroaryl" refers to a mono- or di-cyclic heteroaromatic ring having 5 or 13 ring members and wherein 1, 2, 3 or 4 ring atoms are independently selected from N, O and S. Examples include five-membered ring heteroaryls are thienyl, furyl, pyrrolyl, imidazolyl, thiazolyl, oxazolyl, pyrazolyl, isothiazolyl, isoxazolyl, 1,2, 3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl or six-membered ring heteroaryls are pyridyl, pyrazinyl, pyrimidinyl, triazinyl and pyridazinyl.

As used herein, the term "leaving group" refers to an atom or group capable of being displaced by a nucleophile (e.g. halogen, alkoxycarbonyl, aryloxycarbonyl, mesyloxy, tosyloxy, trifluoromethanesulfnolyoxy, 2,4-dinitrophenoxy, methoxy, p-nitrophenlate, imidazolyl, and the like).

As used herein, the phrase "protecting group" means temporary substituents protecting a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been extensively reviewed (see, e.g. Jarowicki, K.; Kocienski, P. Perkin Trans. 1, 2001, issue 18, p. 2109).

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio and/or that are approved or approvable by a regulatory agency or body, for example the Food and Drug Administration or the European Medicines Agency.

As used herein, the term "salt" refer to forms of the disclosed compounds, wherein the parent compound is modified by making acid or base salts thereof, that possess the desired pharmacological activity of the parent compound. Generally, pharmaceutically acceptable salts of the compound of the invention as defined above may be obtained using standard procedures well known in the art, for example by reacting a sufficiently basic compound, for example an alkyl amine with a suitable acid, for example, hydrochloride or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aq. medium, followed by conventional purification techniques. Such salts include Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like.

As used herein, the terms "crystal" or "crystalline solid" refer to a homogenous solid that is arranged in a definite and repeating three-dimensional pattern of atoms, ions and molecules, with smooth external surfaces with characteristic angles between them. Crystals, as opposed to amorphous solids, have a definite melting point.

As used herein, the term "co-crystal" refer to forms of the disclosed compounds, wherein the disclosed compound together with one or more different compounds (e.g. atoms, ions or molecules) forms a unique single phase, crystalline structure with unique physico-chemical properties as demonstrated by XRPD and/or melting points and/or solubility and/or chemical stability and/or mechanical properties.

As used herein, the term "compounds or pharmaceutically acceptable salts" include hydrates and solvates thereof.

A variety of compound of the invention as defined above may exist in particular geometric or stereoisomeric forms. The present invention takes into account all such compounds, including tautomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. All chiral, diastereomeric and racemic forms are intended, to be included in the scope of the invention, unless the specific stereochemistry or isomeric form is specifically indicated.

As used herein, "tautomer" means other structural isomers that exist in equilibrium resulting from the migration of a hydrogen atom. For example, keto-enol tautomerism occurs where the resulting compound has the properties of both a ketone and an unsaturated alcohol. Compounds and salts/co-crystals described in this specification may be isotopically-labelled compounds (or "radio-labelled"). In that instance, one or more atoms are replaced by an atom having an atomic mass or mass number different from the atomic mass or mass number typically found in nature (i.e., naturally occurring). Examples of suitable isotopes that may be incorporated include $^{2}H$ (also written as "D" for deuterium), $^{3}H$ (also written as "T" for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is used will depend on the specific application of that radio-labelled derivative. For example, for in vitro receptor labelling and competition assays, compounds that incorporate $^{3}H$ or $^{14}C$ are often useful. For radio-imaging applications $^{11}C$ or $^{18}F$ are often useful. In some embodiments, the radionuclide is $^{3}H$. In some embodiments, the radionuclide is $^{14}C$. In some embodiments, the radionuclide is $^{11}C$. And in some embodiments, the radionuclide is $^{18}F$.

Medical Use

The compounds of the present invention are believed to be useful as a medicament in therapy. The compounds are especially believed to be useful in the prevention, progression, prophylaxis and/or treatment of autoimmune diseases and in the diseases selected from the group comprising or containing arthritides associated with or including osteoarthritis or osteoarthrosis, both primary and secondary to dysplasia, such as congenital hip dysplasia, cervical and lumbar spondylitis, low back and neck pain, reactive arthritis, undifferentiated spondyloarthropathy, septic arthritis, infection-related arthopathies and bone disorders, such as tuberculosis, Potts' disease and Poncet's syndrome, acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma, plaque psoriasis, lichen planus, pemphigus vulgaris, cutaneous lupus erythmatosus, alopecia areata, corticosteroid-dependent chronic idiopathic urticaria, pyoderma gangrenosum, with/without IBD, dermatitis herpetiformis, including any juvenile form, mixed connective tissue disease, and undifferentiated connective tissue disease, inflammatory myopathies including dermatomyositis and polymyositis, polymalgia rheumatic, juvenile arthritis including idiopathic inflammatory arthritides of whatever joint distribution and associated syndromes, and rheumatic fever and its systemic complications, vasculitides including giant cell arteritis, Takayasu's arteritis, Churg-Strauss syndrome, polyarteritis nodos, microscopic polyarteritits, and vasculitides associated with viral infection, hypersensitivity reactions, cryoglobulins, and paraproteins, Familial Mediterranean fever, Muckle-Wells syndrome, and Familial Hibernian Fever, Kikuchi disease; drug-induced arthralgia, tendonititides, and myopathies.

The compound of formula I, as defined above, for use in the prevention, progression, prophylaxis and/or treatment of autoimmune diseases, whereby the ratio of pharmacokinetic parameters (Css, Cmax and/or AUC) of sulfapyridine to sulfasalazine in blood plasma after oral administration of the compound as defined above, is smaller than 20, or 10 or 5 or 4, or 3, or 2, or 1.5, or 1.

The compound of formula I, as defined above, for use in the prevention, progression, prophylaxis and/or treatment of autoimmune diseases, whereby the ratio of pharmacokinetic parameters (Css, Cmax and/or AUC) of sulfasalazine to sulfapyridine in blood plasma after oral administration of the compound as defined above, compared to said ratio after oral administration of sulfasalazine, is improved by at least a factor 1.1 to 100, or 1.5 to 50 or 2, or 3, or 5, or 10.

In an embodiment, the ratio of Css of sulfapyridine to sulfasalazine in blood plasma after oral administration of the compound as defined above, compared to said ratio after oral administration of sulfasalazine, is smaller than 20, or 10 or 5 or 4, or 3, or 2, or 1.5, or 1.

In another embodiment, the ratio of Cmax of sulfapyridine to sulfasalazine in blood plasma after oral administration of the compound as defined above, compared to said ratio after oral administration of sulfasalazine, is smaller than 20, or 10 or 5 or 4, or 3, or 2, or 1.5, or 1.

In a further embodiment, the ratio of AUC of sulfapyridine to sulfasalazine in blood plasma after oral administration of the compound as defined above, compared to said ratio after oral administration of sulfasalazine, is smaller than 20, or 10 or 5 or 4, or 3, or 2, or 1.5, or 1.

The route of administration of compounds of the present invention may be orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The optimum dosage and frequency of administration will depend on the particular condition being treated and its severity; the age, sex, size and weight, and general physical condition of the particular patient; other medication the patient may be taking; the route of administration; the formulation; and various other factors known to physicians and others skilled in the art. For example, the frequency of administration will vary for the disease being treated from 1 to 4 times daily. The quantity of the compounds of the invention to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods and uses of the invention.

The compounds of the invention may be used on their own but will generally be administered in the form of a pharmaceutical composition in which the compounds of the invention/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

For preparing pharmaceutical compositions from the compounds of the invention, inert, pharmaceutically acceptable carriers can be either solid or liquid. Solid form compositions include powders, tablets, dispersible granules, capsules, cachets, and suppositories. Liquid forms include parenteral forms for either intravenous or sub cutaneous or intra-muscular administration, or syrups, and liquid capsules for oral administration.

A solid carrier can be one or more substances, which may also act as diluents, flavoring agents, solubilizers, lubricants, suspending agents, binders, or tablet disintegrating agents; it can also be an encapsulating material.

Depending on the mode of administration, the pharmaceutical composition will preferably comprise from 0.05 to 99° wt (percent by weight), more preferably from 0.05 to 90° wt, still more preferably from 0.10 to 70° wt, and even more preferably from 0.10 to 50° wt, of active ingredient, all percentages by weight being based on total composition.

Compounds of the present invention may be used in conjoint therapy with other conventional therapies, which may include one or more agents, such as non-steroidal anti-inflammatory agents (hereinafter NSAIDs), whether applied topically or systemically, including non-selective cyclo-oxygenase COX-1/COX-2 and selective COX-2 inhibitors (such as meloxicam, celecoxib, rofecoxib, valdecoxib, lumarocoxib, parecoxib and etoricoxib), piroxicam, diclofenac, propionic acids (such as naproxen), flurbiprofen, fenoprofen, ketoprofen and ibuprofen, fenamates (such as mefenamic acid), indomethacin, sulindac, ayapropayone, pyrayoleones (such as phenylbutazone), salicylates (such as aspirin); cyclo-oxygenase inhibiting nitric oxide donors (CI-NODs; such as naproxinod); glucocorticosteroids, whether administered by topical, oral, intramuscular, intravenous, or intra-articular routes, (such as flunisolide, triamcinolone acetonide, betamethasone dipropionate, budesonide, fluticasone propionate, ciclesonide or mometasone furoate); methotrexate, leflunomide, hydroxychloroquine, d-penicillamine; auranofin and other parenteral or oral gold preparations;
nutritional supplements such as glucosamine; agonists or antagonists of cytokine function, (including agents which act on cytokine signaling pathways such as modulators of the SOCS system) including alpha-, beta-, and gamma-interferons; insulin-like growth factor type I (IGF-I); interleukins (IL) including IL-1 to 23, and interleukin antagonists or inhibitors (for example diacerein, anakinra, secukinumab, ixekizumab); tumour necrosis factor alpha (TNF-α) inhibitors (such as infliximab, adalimumab, and golimumab) and TNF receptor antagonists including immunoglobulin molecules (such as etanercept) and low-molecular-weight agents such as pentoxifylline; monoclonal antibody targeting B-Lymphocytes (such as CD20 (rituximab). MRA-alL16R and T-Lymphocytes, CTLA4-Ig; HuMax 11-15); modulators of chemokine receptor function, such as an antagonist of CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family; inhibitors of matrix metalloprotease (Tv-IMPs)$_5$ i.e., the stromefysins, the collagenases, and the gelatinases, as well as aggrecanase; especially collagenase-1 (MMP 1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline; leukotriene biosynthesis inhibitors, 5-lipoxygenase (5-LO) inhibitors or 5-lipoxygenase activating protein (FLAP) antagonists (such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones, methoxytetrahydropyrans [e.g. ZD-213S]; SB-210661; pyridinyl-substituted 2-cyanonaphthalene compounds [e.g. L-739,010]; 2-cyanoquinoline compounds [e.g. L-746,530]; indole or quinoline compounds [e.g. MK-591, MK-886, and BAYx1005]; receptor antagonists for leukotrienes (LT) B4, LTC4, LTD4, and LTE4 (such as phenothiazin-3-Is [e.g. L-651,392], amidino compounds [e.g. CGS-25019c], benzoxalamines [e.g. ontazolast], benzenecatboximidamides [e.g. BIIL 284/260], zafirlukast, ablukast, montelukast, pranlukast, verlukast (MK-679), RG-12525, Ro-245913, iralukast (CGP 45715A), and BAYx7195; phosphodiesterase (PDE) inhibitors, such as a methylxanthanine [e.g. theophylline, propentofylline and aminophylline], selective PDE isoenzyme inhibitors including inhibitors of the isoform PDE4 [e.g. apremilast] or inhibitors of PDE5; organophosphate acetylcholinesterase inhibitors (such as metrifonate); endothelin antagonists (such as tezosentan, bosentan, macitentan, enrasentan, and sixtasentan); angiotensin II antagonists (such as azilzartan, losartan, candesartan, and telmisartan); dual antagonists for both angiotensin II and endothelin A receptors (DARAs) such as disclosed in WO2000001389 and WO2001044239; histamine type 1 receptor antagonists (such as cetirizine, loratadine, desloratadine, fexofenadine, acrivastine, terfenadine, astemizole, azelastine, levocabastine, chlorpheniramine, promethazine, cyclizine, or mizolastine), applied orally, topically or parenterally; histamine type 4 receptor antagonists; proton pump inhibitors (such as omeprazole) or a gastroprotective histamine type 2 receptor antagonists; alpha-1/alpha-2 adrenoceptor agonist vasoconstrictor sympathomimetic agents (such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethyl norepinephrine hydrochloride); anticholinergic agents including muscarinic receptor (M1, M2, and M3) antagonist (such as atropine, glycopyrrolate, ipratropium bromide, tiotropium bromide, oxitropium bromide, pirenzepine or telenzepine); beta-adrenoceptor (including beta receptor subtypes 1-4) agonists (such as isoprenaline, salbutamol, formoterol, salmeterol, terbutaline, orciprenaline, bitolterol mesylate, or pirbuterol, or a chiral enantiomer thereof); chromones (such as sodium cromoglycate or nedocromil sodium); agents that modulate a nuclear hormone receptor such as PPARs; immunoglobulin (Ig) or Ig preparations or antagonists or monoclonal antibodies modulating Ig function such as anti-lgE (such as omalizumab); systemic or topically-applied anti-inflammatory agents (such as thalidomide or a derivative thereof, a retinoid, dithranol or calcipotriol); combinations of aminosalicylates and sulfapyridine (such as mesalazine, balsalazide, and olsalazine); immunomodulatory agents such as the thiopurines, e.g. adenosine A2a agonists (such as CGS-21680), adenosine A3 agonists (such as IB-MECA) and adenosine A2b antagonists; antibacterial agents such as a penicillin derivative, a tetracycline, a macrolide, a beta-lactam, a fluoroquinolone, metronidazole, an inhaled aminoglycoside; an antiviral agent (such as acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as lamivudine, stavudine, zalcitabine or zidovudine; or a non-nucleoside reverse transcriptase inhibitor such as nevirapine or efavirenz; cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor; CNS agents such as an antidepressants (such as sertraline), anti-Parkinsonian drugs (such as L-dopa, ropinirole, pramipexole), MAOB inhibitors (such as selegine and rasagiline), COMP inhibitors (such as tasmar), A-2 inhibitors, dopamine reuptake inhibitors, NMDA antagonists, nicotine agonists, dopamine agonists or antagonists, anti-Alzheimer's drugs (such as donepezil, rivastigmine, tacrine); agents for the treatment of acute or chronic pain (such as a centrally or peripherally-acting analgesics [e.g. an opioid or derivative thereof], carbamazepine, phenytoin, sodium valproate, amitryptiline, paracetamol, or a non-steroidal anti-inflammatory agent), parenterally or topically-applied (including inhaled) local anaesthetic agents (such as lidocaine or a derivative thereof); anti-osteoporosis agents, including a hormonal agent (such as raloxifene), and biphosphonates (such as alendronate); tryptase inhibitors; platelet activating factor (PAF) antagonists; interleukin converting enzyme (ICE) inhibitors; IMPDH inhibitors; adhesion molecule inhibitors including VLA-4 antagonists; cathepsin; kinase inhibitors such as an inhibitor of tyrosine kinase (such as Btk, Itk, Jak3 or MAP, [e.g. tofacitinib, gefitinib or imatinib mesylate]), a serine/threonine kinase inhibitors (such as an inhibitor of a MAP kinase such as p38, INK, protein kinase A, B or C, or inhibitors of kappaB kinases, such as IKK1, IKK2 or IKK3), or modulators of kinases involved in cell cycle regulation (such as a cylin-dependent kinase); glucose-6 phosphate dehydrogenase inhibitors; kinin-B.sub1.- or B.sub2.-receptor antagonists; anti-gout agents (such as colchicine); xanthine oxidase inhibitors (such as allopurinol); uricosuric agents (such as probenecid, sulfinpyrazone or benzbromarone); growth hormones (such as secretagogue); transforming growth factor (TGFβ); platelet-derived growth factor (PDGF); fibroblast growth factor (such as basic fibroblast growth factor (bFGF)); granulocyte macrophage colony stimulating factor (GM-CSF); capsaicin cream; tachykinin KK.sub 1. or NK.sub 3. receptor antagonists (such as NKP-608C, SB-233412 (talnetant) or D-441S); elastase inhibitor (such as LT-77 or ZD-0892); TNF-alpha converting enzyme inhibitors (TACE); induced nitric oxide synthase (iNOS) inhibitors; chemoattractant receptor-homologous molecule expressed on TH2 cells, (such as a CRTH2 antagonists); inhibitors of P38; modulators of the function of Toll-like receptors (TLR), modulators of the activity of purinergic receptors such as P2X7; or inhibitors of transcription factor activation (such as NFkB, API, or STATS), agents modulating guanylate cyclase (such as riociguat); agents for the treatment of cancer, for example suitable agents include: an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitroso-urea); an antimetabolite (for example an antifolate such as a fluoropyrimidine like 5-fluorouracil ortegafur, raltitrexed, methotrexate, cytosine arabinoside, hydroxyurea, gemcitabine or paclitaxel); an anti-tumor antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere): or a topoisomerase inhibitor (for example an epipodophyllotoxin such as etoposide, teniposide, amsacrine, topotecan or a camptothecin); a cytostatic agent such as an anti-oestrogen (for example tamoxifen, toremifene, raloxifene, droloxifene or iodoxyfene), an oestrogen receptor down regulator (for example fulvestrant), an antiandrogen (for example bicalutamide, flutamide, or cyproterone acetate), a LHRH antagonist or LHRH agonist (for example goserelin, leuprorelin or triptorelin), a progestogen (for example megestrol acetate), an aromatase inhibitor (for example as anastrozole, letrozole, vorazole or exemestane) or an inhibitor of 5α-reductase such as finasteride; an agent which inhibits cancer cell invasion (for example a metalloproteinase inhibitor like marimastat or an inhibitor of urokinase plasminogen activator receptor function); an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-lnethoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033), an inhibitor of the platelet-derived growth factor family, or an inhibitor of the hepatocyte growth factor family; an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin); a vascular damaging agent such as combretastatin A4, or a compound disclosed in WO 99/02166, WO 00/40529, WO 00/41669, WO 01/92224, WO 02/04434 or WO 02/08213; an agent used in antisense therapy, for example one directed to one of the targets listed above, such as ISIS 2503, an anti-ras antisense; an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitro-reductase enzyme and approaches to increase patient tolerance to chemotherapy or radiotherapy such as multi-drug resistance gene therapy; or an agent used in an immunotherapeutic approach, for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies.

Preparation of Compounds.

Compounds of the present invention can be prepared by the processes described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in Protective Groups in *Organic Synthesis* by T. W. Greene, P. G. M Wutz, 3$^{rd}$ Edition, Wiley-Interscience, New York, 1999.

General Methods

All solvents used were of analytical grade and commercially available anhydrous solvents were routinely used for reactions. Starting materials used were available from commercial sources or prepared according to literature procedures. Room temperature refers to temperatures ranging from 20 to 25° C. Solvent mixture compositions are given as volume percentages or volume ratios. The produced examples were characterized regarding identity, crystal modification, thermal properties, melting point, solubility in water, purity, and hygroscopicity using the following methods:

Thin layer chromatography (TLC) was performed on Merck TLC-plates (Silica gel 60 $F_{254}$) and spots were UV visualized. Straight phase flash column chromatography ("flash chromatography") was manually performed on Merck Silica gel 60 (0.040-0.063 mm).

$^1$H NMR and $^{13}$C NMR spectra were recorded at 298K on a Varian Unity Inova 400 MHz (software: VKMR 6.1C and VNMRJ 1.1D; probe: Xalorac 5 mm DG400-5AT) or a Varian Mercury-VX 300 MHz (software: VNMR 6.1C; probe: Varian 5 mm AutoSW PFG) instrument. The central peaks of acetone-d$_5$ or dimethylsulphoxide (DMSO)-d$_6$ were used as internal references.

X-ray powder diffraction (XRPD) analyses may be performed on samples prepared according to standard methods (see for example Giacovazzo et al., eds., Fundamentals of Crystallography, Oxford University Press (1992); Jenkins & Snyder, eds., Introduction to X-Ray Powder Diffractometry, John Wiley & Sons, New York (1996); Bunn, ed., Chemical Crystallography, Clarendon Press, London (1948); and Klug and Alexander, eds., X-Ray Diffraction Procedures, John Wiley & Sons, New York (1974): Precipitated samples were smeared out on a zero-background sample holder and analysed from 2-35° (2-teta) using a Thermo ARL X'tra diffractometer equipped with a peltier-cooled solid state detector, a Cu tube ($\lambda$=1.5418 Å), 45 kV/44 mA, using spinning sample holders and continuous scans with a scan speed of 2°/min and step size of 0.02°.

Differential scanning calorimetry (DSC) using standard methods, for example those described in Hohne, G. W. H. et al (1996), Differential Scanning Calorimetry, Springer, Berlin, the calometric response of a test sample to increasing temperature was investigated using a PerkinElmer Pyris DSC. The temperature interval was normally 60 to 285° C., with some variations depending on results and need of re-runs. The scanning rate was 10° C./min. About 2 mg sample was used; the measurements were performed using open aluminum pans and dry nitrogen atmosphere to avoid oxidative degradation. It is well known that the DSC onset and peak temperatures may vary due to the purity of the sample and instrumental parameters, especially the temperature scan rate. A person skilled in the art can use routine optimization/calibration to set up instrumental parameters for a DSC so that data comparable to the data presented here can be collected.

Gravimetric vapour sorption (GVS) was used to determine the hygroscopicity of the samples: experiments were performed at 25° C. using a DVS 1 instrument from SMS Ltd to record adsorption-desorption isotherms using different methods, the main features being: a single sorption/desorption cycle from 0 to 80% RH in 10% RH steps with a dm/dt trigger value of 0.002% (dm/dt=change in mass with time–when the balance stability is within this value the next step is automatically started, however, if those conditions are not achieved there is a default maximum time for each step of 6 hours). The sample amount used was 1-3 mg.

The amount of dissolved sulfasalazine was determined by HPLC on an Agilent 1100 instrument, using a Waters XTerra 3.5 µm C18 column (50*4.6 mm) and a mobile phase consisting of 95% ethanol/25 mM phosphoric acid 45/55. The flow rate was 1.0 mL/min, injection volume 5 µL and detection wavelengths 358 nm (for assay) and 260 nm (for chromatographic purity). Quantitation was performed using external standard methodology. The assay method has been validated with respect to selectivity, repeatability and linearity.

Thermal Gravimetric Analysis (TGA) Instrument: PerkinElmer TGA7 Method: About 3 mg of sample was charged into and weighed in an open Pt-pan and analysed, in a flow of dry nitrogen gas to ensure an inert atmosphere, from 22 to 120° C. using a scan speed of 10° C./min, then held at 120° C. for 30 minutes.

Preparative Chromatography:

Preparative chromatography was run on for example a Waters FractionLynx system with an Autosampler combined Automated Fraction Collector (Waters 2767), Gradient Pump (Waters 2525), Column Switch (Waters CFO) and PDA (Waters 2996). Column; XBridge® Prep C8 10 µm OBD™ 19×300 mm, with guard column; XTerra® Prep MS C8 10 µm 19×10 mm Cartridge. A gradient of A (95% 0.1 M NH$_4$OAc in MilliQ water and 5% MeCN) in B (100% MeCN) or a gradient of A (95% 0.1 M NH$_4$OAc in MilliQ water and 5% MeOH), A (0.2% NH$_3$ in MilliQ water) or A (0.2% formic acid in MilliQ water) in B (100% MeOH) was applied for LC-separation at flow rates 20-30 ml/min. Preparative chiral chromatography for separation of isomers was run on for example an LaPrep® system using the specified column and mobile phase system.

LC/MS/MS analysis equipment: API 4000 equipped with an Agilent 1100 HPLC and a Leap Technologies autosampler. A HPLC Phenomenex Onyx Monolithic C18 (CHO-7644) column at a temperature of 35° C., flow rate of 2.0 mL/min, injection volume of 30 uL, and a 3 min run time was used. Mobile phase AI was 01% formic acid in water and Mobile phase AII was 0.1% formic acid in ACN. The gradient was 2% AII in AI at t=0 to t=0.13 min, 5% AII in AI at t=1.4 to 2.2 min and 98% AII in AI at t=2.3 to 3.0 min. The ratio was determined using a negative ion mode (Q1 128.94; Q2 71).

Abbreviations

5-ASA 5-aminosalicylic acid, mesalamine
ACN acetonitrile
Aq. aqueous
DMF N,N-dimethyl formamide
DMSO dimethyl sulfoxide
EtOAc ethyl acetate
EtOH ethanol
eq. or equiv. equivalent
h hour(s)
HPLC high performance liquid chromatography
LCMS liquid chromatography mass spectrometry
MeOH methanol
min minute(s)
MS mass spectrometry
NH$_4$OAc ammonium acetate
NMR nuclear magnetic resonance
r.t. room temperature, i.e. between 16 to 25° C. Celcius
sat. saturated
SP sulfapyridine
SSZ sulfasalazine
TFA trifluoroacetic acid
THF tetrahydrofuran
TLC thin layer chromatography Naming Compounds:

Compounds have been named using CambridgeSoft MedChem ELN v2.2 or ACD/Name, version 10.0, or 10.06, or version 12.01, software from Advanced Chemistry Development, Inc. (ACD/Labs), Toronto ON, Canada, www.acd-labs.com, or Lexichem, version 1.9, software from OpenEye.

General Synthetic Methods

General synthetic methods useful in the synthesis of compounds described herein are available in the art. Starting materials useful for preparing compounds and intermediates thereof and/or practicing methods described herein are commercially available or can be prepared by well-known synthetic methods. The methods presented in the schemes and examples provided by the present disclosure are illustrative rather than comprehensive. It will be apparent to those skilled in the art that many modifications, both to materials and methods, may be practiced without departing from the scope of the disclosure.

For example, a compound of formula I may be obtained via the synthetic methods illustrated in the following steps:
  (i) Sulfasalazine and 1.0 to 1.5 equivalent of base in an organic solvent, such as DMF: stirr for 0.5 to 4 h at 15 to 60° C. (for example room temperature)
  (ii) add 1.0 to 1.5 equivalent of halo-acetamide, such as chloroacetamide or iodoacetamide, in an organic solvent, such as DMF: stir for 10 to 48 h at 60 to 130° C. (for example 85° C.), optionally in the presence of KI.
  (iii) cool, partition between an aqueous saturated NaCl solution and organic solvent, such as ethyl acetate, dry organic solvent with use of anhydrous MgSO4 or Na2SO4 or similar, filtrate and evaporate solvent
  (iv) purifying with use of chromatography and/or crystallization, e.g. using a mixture of ethyl acetate, triethylamine and methanol.

For example, a compound of formula I may be obtained as follows: a solution of sulfasalazine and potassium carbonate (1.0 to 1.5 eq.) in DMF (0.2-1.0 mmol/mL) is stirred for 60 min at r.t., after which a solution of a chloroacetamide (1.0 to 1.5 eq.) in DMF (1.0-2.0 mmol/mL) is added. The reaction mixture is stirred for 17 h at 85° C., after which it is quenched by adding an aq. sat. solution of NaCl (2:1 ratio to DMF). The aq. phase is extracted with EtOAc (10:1 ratio to aq. phase; 3 times), after which the combined org. phases are washed with some aq. sat. solution of NaCl (ca. 3% of the total volume). The residue in the reaction vessel is dissolved in MeOH and added to the EtOAc layer, dried over anhydrous MgSO4, filtrated and evaporated in vacuo. The residue is purified using either flash chromatography or preparative chromatography or crystallization.

The process of preparation of a compound of formula I, as defined above substantially pure compounds are provided, or compounds having a purity of a least 80% by weight, or at least 85% by weight, or at least 90% by weight, or at least 90, 91, 92, 93, 94, 95, 96, 97, 98, 99 or 100% by weight.

EXAMPLES

Below follows a number of illustrative, non-limiting examples of the compounds of the invention.

Example 1

Preparation of Compounds of the Invention of Formula I, where $R^1$ and $R^2$ are Hydrogen and $R^3$ and $R^4$ Together with the Nitrogen Atom to which they are Attached Form a Cyclic Structure 2-morpholino-2-oxoethyl-2-hydroxy-5-((4-(N-(pyridine-2-yl)sulfamoyl)phenyl)diazenyl) benzoate (Compound 1a)

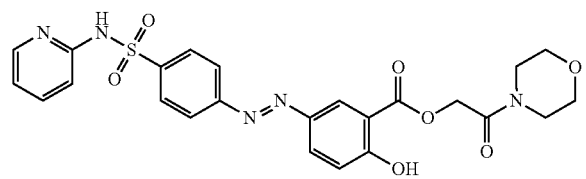 [SMILES: O=C(OCC(=O)N1CCOCC1)c1cc(/N=N/c2ccc(S(=O)(=O)Nc3ccccn3)cc2)ccc1O]

A suspension of 200 mg sulfasalazine and potassium carbonate (1.2 eq.) in DMF (1 mL) is stirred at RT for 1 h, after which a solution of 2-chloro-1-morpholinoethan-1-one (1.2 eq.) in DMF (1 mL) is added. The reaction mixture is stirred for 17 h at 85° C., and poured in EtOAc (40 mL). The EtOAc is washed with a saturated aqueous. solution of NaCl (5 mL) to remove the DMF, while the residue is taken up in MeOH (10 mL). The aq. phase extracted with EtOAc (2×, 40 mL) and the combined org. layers are washed with brine. The combined EtOAc and MeOH layers dried over anhydr. sodium sulfate, filtered and removed in vacuo. The combined EtOAc and MeOH layers dried over anhydr. sodium sulfate, filtered and removed in vacuo. The resulting orange oily residue is purified using flash chromatography over silica with EtOAc(5):MeOH(1) with TEA(0.5%), yielding, after removal of the solvents in vacuo, 133 mg (50.5%) of the title compound as a bright orange solid.

$^1$H-NMR (500 MHz, CD3OD) δ 8.51 (d, J=2.4 Hz, 1H), 8.00-7.91 (m, 6H), 7.76 (m, 1H), 7.53 (d, J=9.2 Hz, 1H), 6.93 (d, J=8.8 Hz, 1H), 6.79 (t, J=6.8 Hz, 1H), 5.15 (s, 2H), 3.76-3.74 (m, 2H), 3.68-3.64 (m, 4H), 3.60-3.58 (m, 2H); MS (ESI): m/z 526.06 (M+H); solubility in de-ionized water at rt after 24 h: >5 mg/mL.

2-(3-methyl-azetidinyl)-2-oxoethyl-2-hydroxy-5-((4-(N-(pyridine-2-yl)sulfamoyl)phenyl)diazenyl) benzoate (Compound 1b)

MS (ESI): m/z 510 (M+H); solubility in de-ionized water at rt after 24 h: >0.5 mg/mL.

2-azetidinyl-2-oxoethyl-2-hydroxy-5-((4-(N-(pyridine-2-yl)sulfamoyl)phenyl)diazenyl) benzoate (Compound 1c)

MS (ESI): m/z 496 (M+H); solubility in de-ionized water at rt after 24 h: >0.5 mg/mL.

2-pyrrolidinyl-2-oxoethyl-2-hydroxy-5-((4-(N-(pyridine-2-yl)sulfamoyl)phenyl)diazenyl) benzoate (Compound 1d)

MS (ESI): m/z 510 (M+H); solubility in de-ionized water at rt after 24 h: >1.5 mg/mL.

2-piperidinyl-2-oxoethyl-2-hydroxy-5-((4-(N-(pyridine-2-yl)sulfamoyl)phenyl)diazenyl) benzoate (Compound 1e)

MS (ESI): m/z 524 (M+H); solubility in de-ionized water at rt after 24 h: >0.5 mg/mL.

2-piperazinyl-2-oxoethyl-2-hydroxy-5-((4-(N-(pyridine-2-yl)sulfamoyl)phenyl)diazenyl) benzoate (Compound 1f)

MS (ESI): m/z 525 (M+H); solubility in de-ionized water at rt after 24 h: >3 mg/mL.

2-azepenyl-2-oxoethyl-2-hydroxy-5-((4-(N-(pyridine-2-yl)sulfamoyl)phenyl)diazenyl) benzoate (Compound 1g)

MS (ESI): m/z 539 (M+H); solubility in de-ionized water at rt after 24 h: >2.5 mg/mL.

Compounds 1b-1 g were prepared as described in detail for compound 1a, providing these title compounds as bright orange solids, in yields ranging from 42-60%

Example 2

Preparation of of Compounds of the Invention of Formula I, where $R^1$, $R^2$ and $R^3$ are Hydrogen and $R^4$ is not Hydrogen 2-(methylamino)-2-oxoethyl-2-hydroxy-5-((4-(N-(pyridine-2-yl)sulfamoyl)phenyl)diazenyl) benzoate (Compound 2a)

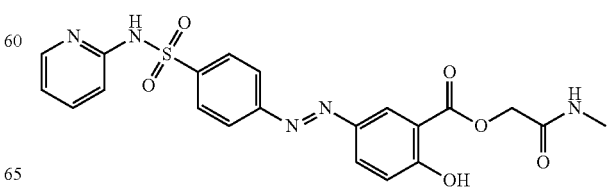

A suspension of 320 mg sulfasalazine and potassium carbonate (1.2 eq.) in DMF (2 mL) is stirred at RT for 1 h, after which a solution of 2-chloro-N-cyclopentylacetamide (1.2 eq.) in DMF (1 mL) is added. The reaction mixture is stirred for 17 h at 85° C., and poured in EtOAc (40 mL). The EtOAc is washed with a saturated aqueous. solution of NaCl (5 mL) to remove the DMF, while the residue is taken up in MeOH (10 mL). The aq. phase extracted with EtOAc (2×, 40 mL) and the combined org. layers are washed with brine. The combined EtOAc and MeOH layers dried over anhydr. sodium sulfate, filtered and removed in vacuo. The resulting orange oily residue is purified using reversed gradient flash chromatography over silica with starting with an aq. buffer (pH 8, 95%) and ACN (5%) to 95% ACN over 20 min, yielding 308 mg (84.2%) of the title compound after evaporation of the ACN and freeze-drying, as a bright orange solid.

$^1$H-NMR (500 MHz, CD3OD) δ 8.51 (d, J=2.4 Hz, 1H), 8.00-7.91 (m, 6H), 7.77-7.74 (m, 1H), 7.53 (d, J=9.0 Hz, 1H), 6.93 (d, J=8.8 Hz, 1H), 6.77 (t, J=6.7 Hz, 1H), 4.87 (s, 2H), 2.75 (s, 3H);

MS (ESI): m/z 470 (M+H), 468 (M−H); solubility in de-ionized water at rt after 24 h: >5 mg/mL.

2-(ethylamino)-2-oxoethyl-2-hydroxy-5-((4-(N-(pyridine-2-yl)sulfamoyl)phenyl)diazenyl) benzoate (Compound 2b)

MS (ESI): m/z 584.12 (M+H); solubility in de-ionized water at rt after 24 h: >1 mg/mL.

2-(propylamino)-2-oxoethyl-2-hydroxy-5-((4-(N-(pyridine-2-yl)sulfamoyl)phenyl)diazenyl) benzoate (Compound 2c)

MS (ESI): m/z 498 (M+H); solubility in de-ionized water at rt after 24 h: >1 mg/mL.

2-(isopropylamino)-2-oxoethyl-2-hydroxy-5-((4-(N-(pyridine-2-yl)sulfamoyl)phenyl)diazenyl) benzoate (Compound 2d)

MS (ESI): m/z 498.1 (M+H); solubility in de-ionized water at rt after 24 h: >1 mg/mL.

2-(isobutylamino)-2-oxoethyl-2-hydroxy-5-((4-(N-(pyridine-2-yl)sulfamoyl)phenyl)diazenyl) benzoate (Compound 2e)

MS (ESI): m/z 512.0 (M+H); solubility in de-ionized water at rt after 24 h: >5 mg/mL.

2-((cyclopropylmethyl)amino)-2-oxoethyl-2-hydroxy-5-((4-(N-(pyridine-2-yl)sulfamoyl)phenyl)diazenyl) benzoate (Compound 2f)

MS (ESI): m/z 512 (M+H); solubility in de-ionized water at rt after 24 h: >1 mg/mL.

2-cyclopentylamino)-2-oxoethyl-2-hydroxy-5-((4-(N-(pyridine-2-yl)sulfamoyl)phenyl)diazenyl) benzoate (Compound 2g)

MS (ESI): m/z 524.0 (M+H); solubility in de-ionized water at rt after 24 h: >1 mg/mL.

2-(2-methoxylethyl)amino)-2-oxoethyl-2-hydroxy-5-((4-(N-(pyridine-2-yl)sulfamoyl)phenyl)diazenyl) benzoate (Compound 2h)

MS (ESI): m/z 514 (M+H); solubility in de-ionized water at rt after 24 h: >0.5 mg/mL.

Compounds 2b-2h were prepared as described in detail for compound 2a, providing these title compounds as bright orange solids, in yields ranging from 35-57%.

Example 3

Preparation of Compounds of the Invention of Formula I, where R$^1$ and R$^2$ are Hydrogen and R$^3$ is R$^4$ is not Hydrogen.

2-(dimethylamino)-2-oxoethyl-2-hydroxy-5-((4-(N-(pyridine-2-yl)sulfamoyl)phenyl)diazenyl) benzoate (Compound 3a)

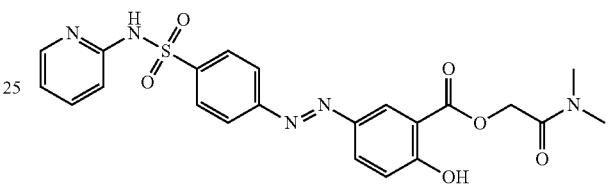

A suspension of 320 mg sulfasalazine and potassium carbonate (1.2 eq.) in DMF (2 mL) is stirred at RT for 1 h, after which a solution of 2-chloro-N-cyclopentylacetamide (1.2 eq.) in DMF (1 mL) is added. The reaction mixture is stirred for 17 h at 85° C., and poured in EtOAc (40 mL). The EtOAc is washed with a saturated aqueous. solution of NaCl (5 mL) to remove the DMF, while the residue is taken up in MeOH (10 mL). The aq. phase extracted with EtOAc (2×, 40 mL) and the combined org. layers are washed with brine. The combined EtOAc and MeOH layers dried over anhydr. sodium sulfate, filtered and removed in vacuo. The resulting orange oily residue is purified using reversed gradient flash chromatography over silica with starting with an aq. buffer (pH 8, 95%) and ACN (5%) to 95% ACN over 20 min, yielding 319 mg (66.3%) of the title compound after evaporation of the ACN and freeze-drying, as a bright orange solid.

$^1$H-NMR (500 MHz, CD3OD) δ 8.51 (m, 1H), 7.99-7.89 (m, 6H), 7.75 (m, 1H), 7.53 (m, 1H), 6.94 (m, 1H), 6.79 (m, 1H), 5.12 (s, 2H), 3.16 (s, 3H), 2.96 (s, 3H); MS (ESI): m/z 484 (M+H); solubility in de-ionized water at rt after 24 h: >0.5 mg/mL.

2-(diethylamino)-2-oxoethyl-2-hydroxy-5-((4-(N-(pyridine-2-yl)sulfamoyl)phenyl)diazenyl) benzoate (Compound 3b)

MS (ESI): m/z 512.09 (M+H); solubility in de-ionized water at rt after 24 h: >1 mg/mL.

2-(dipropylamino)-2-oxoethyl-2-hydroxy-5-((4-(N-(pyridine-2-yl)sulfamoyl)phenyl)diazenyl) benzoate (Compound 3c)

MS (ESI): m/z 512.09 (M+H); solubility in de-ionized water at rt after 24 h: >1 mg/mL.

2-(dibutylamino)-2-oxoethyl-2-hydroxy-5-((4-(N-(pyridine-2-yl)sulfamoyl)phenyl)diazenyl) benzoate (Compound 3d)

MS (ESI): m/z 512.09 (M+H); solubility in de-ionized water at rt after 24 h: >1 mg/mL.

2-(di-(1-methylethylamino))-2-oxoethyl-2-hydroxy-5-((4-(N-(pyridine-2-yl)sulfamoyl)phenyl)diazenyl) benzoate (Compound 3e)

MS (ESI): m/z 512.09 (M+H); solubility in de-ionized water at rt after 24 h: >1 mg/mL.

Compounds 3b-3e were prepared as described in detail for compound 3a, providing these title compounds as bright orange solids, in yields ranging from 45-70%.

Example 4

Preparation of Compounds of the Invention of Formula I, where $R^1$ and $R^2$ are Hydrogen and $R^3$ is not $R^4$ and Neither $R_3$ Nor $R_4$ is Hydrogen

2-(ethyl(methyl)amino)-2-oxoethyl-2-hydroxy-5-((4-(N-(pyridine-2-yl)sulfamoyl)phenyl)diazenyl) benzoate (Compound 4a)

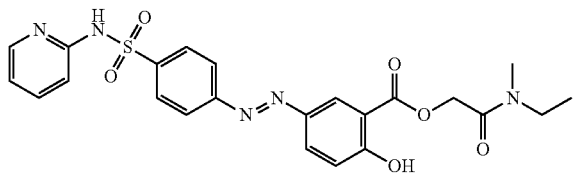 [SMILES: CCN(C)C(=O)COC(=O)c1cc(/N=N/c2ccc(S(=O)(=O)Nc3ccccn3)cc2)ccc1O]

A suspension of 100 mg sulfasalazine and potassium carbonate (1.2 eq.) in DMF (2 mL) is stirred at RT for 1 h, after which a solution of 2-chloro-N-cyclopentylacetamide (1.2 eq.) in DMF (1 mL) is added. The reaction mixture is stirred for 17 h at 85° C., and poured in EtOAc (40 mL). The EtOAc is washed with a saturated aqueous. solution of NaCl (5 mL) to remove the DMF, while the residue is taken up in MeOH (10 mL). The aq. phase extracted with EtOAc (2×, 40 mL) and the combined org. layers are washed with brine. The combined EtOAc and MeOH layers dried over anhydr. sodium sulfate, filtered and removed in vacuo. The resulting orange oily residue is purified using flash chromatography over silica with EtOAc(5):MeOH(1) with TEA(0.5%), yielding, after removal of the solvents in vacuo, 39 mg (31.1%) of the title compound as a bright orange solid.

$^1$H-NMR (500 MHz, CD3OD) δ 8.51 (m, 1H), 8.01-7.89 (m, 6H), 7.76 (m, 1H), 7.59-7.52 (m, 1H), 6.93 (m, 1H), 6.78 (m, 1H), 5.11 (ds, J=7.6 Hz, 2H), 3.49-3.40 (m, 2H), 3.0 (ds, J=7.3 Hz, 3H), 1.26-1.10 (dt, J=65.7, 7.2 Hz, 6H); $^{13}$C-NMR (101 MHz, CD3OD) δ 175.04, 167.39, 167.24, 156.94, 156.91, 155.88, 155.86, 146.13, 145.45, 145.30, 143.15, 143.10, 143.07, 143.03, 129.16, 128.50, 127.51, 123.57, 123.53, 123.51, 120.53, 118.35, 118.08, 118.01, 113.01, 112.92, 55.23, 55.08, 45.34, 44.43, 34.69, 33.75, 13.50, 12.52; MS (ESI): m/z 498.05 (M+H); solubility in de-ionized water at rt after 24 h: >1 mg/mL

N-methyl-N-2-methylethylamino-2-oxoethyl-2-hydroxy-5-((4-(N-(pyridine-2-yl)sulfamoyl)phenyl) diazenyl) benzoate (Compound 4b)

MS (ESI): m/z 512 (M+H); solubility in de-ionized water at rt after 24 h: >0.5 mg/mL.

N-butyl-N-methylamino)-2-oxoethyl-2-hydroxy-5-((4-(N-(pyridine-2-yl)sulfamoyl)phenyl) diazenyl) benzoate (Compound 4c)

MS (ESI): m/z 526 (M+H); solubility in de-ionized water at rt after 24 h: >1 mg/mL.

N-methyl-N-(2,2-dimethylpropyl)amino-2-oxoethyl-2-hydroxy-5-((4-(N-(pyridine-2-yl)sulfamoyl)phenyl)diazenyl)benzoate (Compound 4d)

MS (ESI): m/z 540 (M+H); solubility in de-ionized water at rt after 24 h: >0.1 mg/L.

N-butyl-N-ethylamino-2-oxoethyl-2-hydroxy-5-((4-(N-(pyridine-2-yl)sulfamoyl)phenyl) diazenyl)benzoate (Compound 4e)

MS (ESI): m/z 540 (M+H); solubility in de-ionized water at rt after 24 h: >0.5 mg/mL.

N-cyclohexyl-N-methylamino-2-oxoethyl-2-hydroxy-5-((4-(N-(pyridine-2-yl)sulfamoyl)phenyl) diazenyl)benzoate (Compound 4f)

MS (ESI): m/z 556 (M+H); solubility in de-ionized water at rt after 24 h: >0.1 mg/mL.

N-ethyl-N-cyclohexylamino-2-oxoethyl-2-hydroxy-5-((4-(N-(pyridine-2-yl)sulfamoyl)phenyl) diazenyl) benzoate (Compound 4g)

MS (ESI): m/z 570 (M+H); solubility in de-ionized water at rt after 24 h: >0.1 mg/mL.

N-(2-(methylethyl)-N-(2,2-dimethylpropyl)amino-2-oxoethyl-2-hydroxy-5-((4-(N-(pyridine-2-yl)sulfamoyl)phenyl)diazenyl)benzoate (Compound 4h)

MS (ESI): m/z 568 (M+H); solubility in de-ionized water at rt after 24 h: >0.5 mg/mL.

Compounds 4b-4h were prepared as described in detail for compound 4a, providing these title compounds as bright orange solids, in yields ranging from 30-55%.

For a prodrug, it can be desirable that it remains intact while in the gastrointestinal tract and be transformed into the parent drug after being absorbed or taken up from the gastrointestinal lumen, e.g. in either the enterocytes lining of the gastrointestinal lumen or in the blood. A useful level of stability can at least in part be determined by the mechanism of transformation and pharmacokinetics of the prodrug. In general, prodrugs that are more stable in gastrointestinal wash assays and are more labile in intestinal S9 fraction, and/or plasma, and/or liver S9 fraction can be useful as an orally administered prodrug. In general, prodrugs that are more stable in a range of pH physiological buffers (pH 1 to 8) can be more useful as prodrugs. The results of tests, such as those described in examples 5 and 6, for determining the enzymatic or chemical cleavage of prodrugs in vitro can be used to select prodrugs for in vivo testing. The stabilities of prodrugs can be evaluated in one or more in vitro systems using a variety of preparations following methods known in the art. For example, methods used to determine the stability of prodrugs in aq. buffers (pH 1 to 8) as well as in plasma, liver S9 and intestine S9 preparations, or colonic wash assays have been extensively described in the literature and are offered by commercial vendors.

Example 5

Methods for Determining the Chemical Stability of Compounds 1a to 4h In Vitro.
Preparation of Aq. Buffers and Stability Study For the pH 1 stability study (mimic gastric pH), 190 uL of 0.1 M HCl is added to 10 uL of a 20 mM aq. solution of test compound. The samples are incubated for 60 and 120 min at 37° C.

Following the incubation, the samples cooled to room temperature and 800 uL of a 50% ACN in water is added to the samples. The samples are analyzed using LC/MS/MS to determine the ratio of ester pro-drug vs sulfasalazine.

For the pH 6.8 stability study (mimic upper GI tract/small intestine pH), an aq. buffer is prepared using 6.805 g $KH_2PO_4$ and 0.896 g NaOH per 1.0 L $H_2O$. The buffer (190 uL) is added to a 20 mM aq. solution of test compound. The samples are incubated for 30 and 60 min at 37° C. Following the incubation, the samples cooled to room temperature and 800 uL of a 50% ACN in water is added to the samples. The samples are analyzed using LC/MS/MS to determine the ratio of ester pro-drug vs sulfasalazine.

For the pH 8.0 stability study (mimic colon pH), an aq. buffer is prepared using 1.5 g ammonium acetate and 4.25 mL of an 0.25 M ammonium hydroxide solution per 1.0 L $H_2O$.

The buffer (190 uL) is added to a 20 mM aq. solution of test compound. The samples are incubated for 30 and 60 min at 37° C. Following the incubation, the samples cooled to room temperature and 800 uL of a 50% ACN in water is added to the samples. The samples are analyzed using LC/MS/MS to determine the ratio of ester pro-drug vs sulfasalazine.

Results Compounds 1a to 4h are stable under acidic (pH 1), neutral (pH 6.8) and basic (pH 8) conditions for at least 60 min.

Example 6

Methods for Determining the Biological Stability of Compounds 1a to 4h In Vitro.
Preparation of Lysates and Study Protocol Preparation of 400 uM test compound in 0.1 M Tris buffer, pH 7.4: 10 uL of a 20 mM aq. stock solution is added to 490 mL of 0.1 M Tris buffer, pH 7.4 and kept at −20° C. until the time of use.

Enzymatic stability assay: 90 uL per time point of lysate (rat plasma, human plasma) is aliquoted to designated tubes on a cluster plate (t=0 s, 60 s, 5 min, 20 min and 60 min) and preincubated for 10 min at 37° C. For the t=0 s, 90 uL of lysate is added to 200 uL of ice cold 100% ethanol, after which the sample is thoroughly mixed. To this mixture, 10 uL of a 10 uM test compound solution in TRIS buffer, pH 7.4 is added. The sample is mixed again and kept at −20° C. until the time of analysis. For the other time points, 10 uM test compound solutions in TRIS buffer, pH 7.4 is added and 100 uL of the resulting 1 uM lysate-test mixture that is kept at 37° C. is withdrawn at the appropriate time points and added to 200 uL of ice cold 100% ethanol. The mixtures are thoroughly mixed and kept at −20° C. until the time of analysis. For analysis, the samples are defrosted and centrifuged for 10 min at 6000 rpm at 4° C., after which the supernatant is transferred to individual vials suitable for use in the LC-MS/MS equipment. Samples are analyzed with LC-MS/MS to determine the parent prodrug cleavage.
Results Compounds 1a-4h are stable in rat and human plasma for at least 60 min.

For a prodrug of sulfasalazine, it is desirable that the systemic exposure to sulfasalazine versus the systemic exposure to sulfapyridine is changed in favour of sulfasalazine. A useful insight in the systemic exposure levels can be obtained by following the pharmacokinetics of both sulfasalazine and sulfapyridine after administration of the prodrug compounds. In general, prodrugs of sulfasalazine that are more readily absorbed after oral administration than sulfasalazine itself will exhibit a favourable sulfasalazine-sulfapyridine ratio, as less prodrug is available for azide-hydrolysing gut flora. Non-clinical in vivo studies in rodents have been extensively described in the literature and are offered by commercial vendors. The PK parameters found after oral administration of test compounds and sulfasalazine, such as Cmax, Tmax and AUC of sulfasalazine and sulfapyridine in in vivo studies, as presented in example 7, can be used to select prodrugs for further clinical development.

Example 7

Animal Model for Assessing Pharmacokinetics of Compounds of the Invention Versus Sulfasalazine in Rat Following Intravenous or Oral Administration.
List of Abbreviations AUCinf.: Area under the curve to infinity; AUClast.: Area under the curve to the last data point; Cmax: Maximum concentration; CMC: cyclic methyl cellulosa; F: bioavailability; i.v.: intra venous, LC: liquid chromatography; MS: mass spectrometry; NCA: non-compartmental analysis; PK: pharmacokinetic; p.o: per os; SSZ: Sulfasalazine; TI: Test Item; Tmax: Time of maximum concentration; $T_{1/2}$: half life
In Vivo Study Protocol In accordance with Swedish legislations for preclinical in vivo studies in rodents and following evaluation and approval of the experimental procedures the local ethical committee (M388-12), following acclimatization to the housing conditions for a minimum of 7 days after arrival, male Wistar (Hannover) rats (Taconic, Denmark), average weight 300 g; average age 8-10 weeks, were treated with test items (see table 1); 12-16 h prior to dosing all food except for an amount equivalent to a half day consumption was removed. Sulfasalazine (40 mg/kg) and the test items (1 eq) were suspended/dissolved in a 0.5% CMC in phosphate buffer (pH 7.4) and administered using a soft gavage tube in a volume of 10 mL/kg (p.o.). The rats were conscious during sample collection and the blood was taken from the sub-lingual vein. Blood samples were collected from each rat over a period of up to 24 h. At each time point two aliquots of 50 μL each was added to a vial containing 150 μL of sterile water. The samples were mixed immediately and stored in −18° C. until preparation for bioanalysis commenced. All formulations were prepared on the same day that dosing took place. The body weight of the rat was recorded before dosing. The weight of the syringe was recorded before and after administration to allow calculation of the actual amount of test sample delivered. Actual dose administered was used during the evaluation of the data.

Bioanalysis

The plasma levels of sulfasalazine were determined using LCMS/MS in mrm (multiple reaction monitoring) mode.

Samples and standards were injected by a HTC PAL from CTC analytics into an LC system from Shimadzu consisting of a high pressure gradient system of two LC-10 AD pumps controlled by a SCL-10A controller from Shimadzu. The samples were separated using reverse-phase chromatography with gradient elution at a flow rate of 0.8 mL/min. Mobile phases were A:94.9/5/0.1 water/acetonitrile/formic acid and B:5/94.9/0.1 water/acetonitrile/formic acid. Gradient started at 0% B and increased linearly to 100% B in 4 minutes, 100% B was kept for 0.5 minutes and then the system returned to 0% B in 0.1 minutes. The system was equilibrated for 1.4 minutes until the total run time of 6 minutes. The eluent was analyzed by a Quattro Ultima from Micromass equipped with an electrospray ion source. Data was collected and calibrations were calculated by MassLynx 4.0 software. Sulfasalazine was separated on a Waters Symmetry C18 50×2.1 column. The eluent was ionized by negative ion electrospray and the mrm transition from 397 to 197 m/z was monitored.

The diluted blood sample (50 µL blood, 150 µL water) was thawed and mixed. 400 µL of acetonitrile, to precipitate the protein was added and mixed again. The sample was centrifuged at 5000 g for 5 minutes. 100 µL of the supernatant was transferred to a 300 µL glass vial and 100 µL of water was added to reduce the acetonitrile concentration.

Positive and negative mode MS/MS was employed for sulfasalazine. The concentration of the standard curve was in the range from 5 nM to 15625 nM. Samples with analyte concentrations above the upper limit of quantification were diluted with matrix to reach within the assay range. A non-compartmental analysis (NCA) was performed using the Phoenix WinNonLin analysis tool.

Results

TABLE 1

Solubility over time in PBC buffer (pH 7.4) and sulfapyridine/sulfasalazine ratios in plasma following oral administration of sulfasalazine or test compound

| Group | Appearance of test formulations | | Ratio SP to SSZ for | |
|---|---|---|---|---|
| | t = 0 h | t = 4 h[1] | $C_{max}$ (nmol/L)[1] | $AUC_{0-4\,h}$ (h*nmol/L)[1] |
| SSZ | suspension | suspension | 20:1 | 14:1 |
| 1a | clear solution | clear solution | 2:1 | 2:1 |
| 2a | clear solution | clear solution | 11:1 | 11:1 |
| 2d | clear solution | clear solution | 2:1 | 2:1 |
| 2f | clear solution | milky | 2:1 | 6:1 |
| 2h | clear solution | clear solution | 6:1 | 8:1 |
| 3a | clear solution | milky | 5:1 | 6:1 |
| 3b | clear solution | clear solution | 5:1 | 8:1 |
| 4a | clear solution | clear solution | 7:1 | 7:1 |

[1]Following oral administration of 40 mg/kg of Sulfasalazine, the $T_{max}$ for SP is 4 h, while the $T_{max}$ for SSZ is 0.25 h.

The invention claimed is:

1. A compound of formula I, a pharmaceutically acceptable salt, crystals and/or co-crystal thereof, diastereomer, enantiomer, or mixture thereof, wherein:

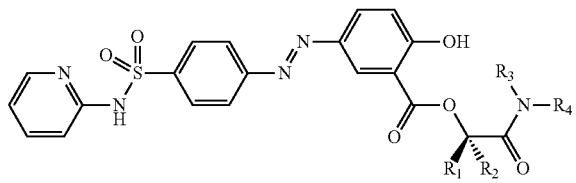

I $R^1$ and $R^2$ are independently chosen from hydrogen and $C_{1-6}$alkyl, $R^3$ and $R^4$ are independently chosen from hydrogen, $C_{1-6}$alkyl, $C_{1-6}$heteroalkyl, $C_{3-12}$cycloalkyl, $C_{3-12}$heterocycloalkyl, $C_{5-13}$aryl, $C_{5-13}$heteroaryl, $C_{3-12}$cycloalkyl$C_{1-6}$alkyl, $C_{3-12}$heterocycloalkyl$C_{1-6}$alkyl, $C_{5-13}$aryl$C_{1-6}$alkyl and $C_{5-13}$heteroaryl$C_{1-6}$alkyl, or $R^3$ and $R^4$ together with the nitrogen to which they are attached form a ring chosen from $C_{3-12}$heterocycloalkyl and $C_{5-13}$heteroaryl, and wherein $R^1$, $R^2$, $R^3$ and $R^4$ are optionally substituted with one or more R, and R is independently chosen from halogen, —OH, —SH, —CN, —CF$_3$, =O, —NO$_2$, —C(O)NR$^5$R$^6$, —R$^5$, —OR$^5$, —SR$^5$, —C(O)R$^5$, —COOR$^5$ and —NR$^5$R$^6$, wherein R$^5$ and R$^6$ are independently chosen from hydrogen, $C_{1-4}$alkyl and $C_{1-4}$cycloalkyl, and optionally substituted with one or more R$^7$, wherein R$^7$ is chosen from halogen, —OH, —SH, —CN, —CF$_3$, =O, —NO$_2$, —C(O)NR$^8$R$^9$, —R$^8$, —OR$^8$, —SR$^8$, —C(O)R$^8$, —COOR$^8$ and —NR$^8$R$^9$, wherein R$^8$ and R$^9$ are independently chosen from hydrogen, $C_{1-4}$alkyl and $C_{1-4}$cycloalkyl.

2. The compound according to claim 1, wherein $R^1$ and $R^2$ are hydrogen, $R^3$ and $R^4$ are independently chosen from hydrogen, $C_{1-4}$alkyl, $C_{1-4}$heteroalkyl, $C_{3-7}$cycloalkyl, $C_{3-7}$heterocycloalkyl, $C_{5-6}$aryl, $C_{5-6}$heteroaryl, $C_{3-6}$cycloalkyl$C_{1-4}$alkyl, $C_{3-6}$heterocycloalkyl$C_{1-4}$alkyl, $C_{5-6}$aryl$C_{1-4}$alkyl and $C_{5-6}$heteroaryl$C_{1-4}$alkyl, or $R^3$ and $R^4$ together with the nitrogen to which they are attached form a ring chosen from $C_{3-8}$heterocycloalkyl and $C_{5-6}$heteroaryl, and wherein $R^1$, $R^2$, $R^3$ and $R^4$ are optionally substituted with one or more R. R is independently chosen from halogen, —OH, —SH, —CN, —CF$_3$, =O, —NO$_2$, —C(O)NR$^5$R$^6$, —R$^5$, —OR$^5$, —SR$^5$, —C(O)R$^5$, —COOR$^5$ and —NR$^5$R$^6$, wherein R$^5$ and R$^6$ are independently chosen from hydrogen, $C_{1-4}$alkyl and $C_{1-4}$cycloalkyl, and optionally substituted with one or more R$^7$, wherein R$^7$ is chosen from halogen, —OH, —SH, —CN, —CF$_3$, =O, —NO$_2$, —C(O)NR$^8$R$^9$, —R$^8$, —OR$^8$, —SR$^8$, —C(O)R$^8$, —COOR$^8$ and —NR$^8$R$^9$, wherein R$^8$ and R$^9$ are independently chosen from hydrogen, $C_{1-4}$alkyl and $C_{1-4}$cycloalkyl.

3. The compound according to claim 2, wherein $R^1$ and $R^2$ are hydrogen, $R^3$ and $R^4$ are independently chosen from hydrogen, $C_{1-6}$alkyl, $C_{3-12}$cycloalkyl, $C_{3-12}$cycloalkyl$C_{1-6}$alkyl, or $R^3$ and $R^4$ together with the nitrogen to which they are attached form a ring chosen from $C_{3-12}$heterocycloalkyl; and wherein $R^3$ and $R^4$ are optionally substituted with one or more R, and R is —OR$^5$ or R$^5$ wherein R$^5$ is $C_{1-4}$alkyl.

4. The compound according to claim 2, wherein $R^1$, $R^2$ and $R^3$ are hydrogen.

5. The compound according to claim 2, wherein $R^1$, $R^2$ and $R^3$ are hydrogen and $R^4$ is methyl, ethyl, propyl, isopropyl, butyl, isobutyl, 2-hydroxyethyl, 2-methoxyethyl, cyclopentyl or cyclopropylmethyl.

6. A compound or a pharmaceutically acceptable salt, crystals or co-crystal thereof, selected from the group comprising 2-morpholino-2-oxoethyl-(E)-2-hydroxy-5-((4-(N-(pyridine-2-yl) sulfamoyl)phenyl)diazenyl)benzoate,
2-(3-methyl-azetidinyl)-2-oxoethyl-2-hydroxy-5-((4-(N-(pyridine-2-yl)sulfamoyl)phenyl) diazenyl)benzoate,
2-azetidinyl-2-oxoethyl-2-hydroxy-5-((4-(N-(pyridine-2-yl)sulfamoyl)phenyl)diazenyl) benzoate,
2-pyrrolidinyl-2-oxoethyl-2-hydroxy-5-((4-(N-(pyridine-2-yl) sulfamoyl)phenyl)diazenyl) benzoate,
2-piperidinyl-2-oxoethyl-2-hydroxy-5-((4-(N-(pyridine-2-yl)sulfamoyl)phenyl)diazenyl) benzoate,
2-piperazinyl-2-oxoethyl-2-hydroxy-5-((4-(N-(pyridine-2-yl)sulfamoyl)phenyl)diazenyl) benzoate, and
2-azepanyl-2-oxoethyl-2-hydroxy-5-((4-(N-(pyridine-2-yl) sulfamoyl)phenyl)diazenyl) benzoate.

7. A compound or a pharmaceutically acceptable salt, crystals or co-crystal thereof, selected from
2-(ethylamino)-2-oxoethyl-2-hydroxy-5-((4-(N-(pyridine-2-yl)sulfamoyl)phenyl)diazenyl) benzoate,
2-(isobutylamino)-2-oxoethyl-2-hydroxy-5-((4-(N-(pyridine-2-yl) sulfamoyl)phenyl)diazenyl) benzoate,
2-(cyclopentylamino)-2-oxoethyl-2-hydroxy-5-((4-(N-(pyridine-2-yl)sulfamoyl)phenyl) diazenyl)benzoate,
2-(methylamino)-2-oxoethyl-2-hydroxy-5-((4-(N-(pyridine-2-yl) sulfamoyl)phenyl) diazenyl)benzoate,
2-(isopropylamino)-2-oxoethyl-2-hydroxy-5-((4-(N-(pyridine-2-yl)sulfamoyl)phenyl)diazenyl) benzoate,
2-((cyclopropylmethyl)amino)-2-oxoethyl-2-hydroxy-5-((4-(N-(pyridine-2-yl)sulfamoyl) phenyl)diazenyl)benzoate,
2-(propylamino)-2-oxoethyl-2-hydroxy-5-((4-(N-(pyridine-2-yl) sulfamoyl)phenyl)diazenyl)benzoate,
2-((2-methoxylethyl)amino)-2-oxoethyl-2-hydroxy-5-((4-(N-(pyridine-2-yl)sulfamoyl)phenyl)diazenyl) benzoate,
2-(dimethylamino)-2-oxoethyl-2-hydroxy-5-((4-(N-(pyridine-2-yl)sulfamoyl)phenyl)diazenyl) benzoate,
2-(diethylamino)-2-oxoethyl-2-hydroxy-5-((4-(N-(pyridine-2-yl) sulfamoyl)phenyl)diazenyl) benzoate,
2-(dipropylamino)-2-oxoethyl-2-hydroxy-5-((4-(N-(pyridine-2-yl) sulfamoyl)phenyl)diazenyl) benzoate,
2-(dibutylamino)-2-oxoethyl-2-hydroxy-5-((4-(N-(pyridine-2-yl) sulfamoyl)phenyl)diazenyl) benzoate, and
2-(di-(1-methylethylamino))-2-oxoethyl-2-hydroxy-5-((4-(N-(pyridine-2-yl) sulfamoyl)phenyl) diazenyl) benzoate.

8. A compound, or a pharmaceutically acceptable salt or co-crystal thereof, selected from
N-ethyl-N-methylamino-2-oxoethyl-2-hydroxy-5-((4-(N-(pyridine-2-yl)sulfamoyl)phenyl) diazenyl)benzoate,
N-methyl-N-2-methylethylamino-2-oxoethyl-2-hydroxy-5-((4-(N-(pyridine-2-yl)sulfamoyl)phenyl)diazenyl) benzoate,
N-butyl-N-methylamino)-2-oxoethyl-2-hydroxy-5-((4-(N-(pyridine-2-yl) sulfamoyl)phenyl) diazenyl)benzoate,
N-methyl-N-(2,2-dimethylpropyl)amino-2-oxoethyl-2-hydroxy-5-((4-(N-(pyridine-2-yl)sulfamoyl)phenyl)diazenyl)benzoate,
N-butyl-N-ethylamino-2-oxoethyl-2-hydroxy-5-((4-(N-(pyridine-2-yl) sulfamoyl)phenyl) diazenyl)benzoate,
N-cyclohexyl-N-methylamino-2-oxoethyl-2-hydroxy-5-((4-(N-(pyridine-2-yl) sulfamoyl)phenyl) diazenyl) benzoate,
N-ethyl-N-cyclohexylamino-2-oxoethyl-2-hydroxy-5-((4-(N-(pyridine-2-yl) sulfamoyl)phenyl) diazenyl) benzoate, and
N-(2-(methylethyl)-N-(2,2-dimethylpropyl)amino-2-oxoethyl-2-hydroxy-5-((4-(N-(pyridine-2-yl)sulfamoyl) phenyl)diazenyl)benzoate.

9. The compound according to claim 1, wherein the ratio of $C_{SS}$, $C_{max}$ and/or AUC of sulfapyridine to sulfasalazine in blood plasma after oral administration to a subject of the compound, compared to said ratio after oral administration of sulfasalazine to the subject, is decreased at least by a factor of 1.5.

10. A pharmaceutical composition comprising the compound according to claim 1 or a pharmaceutically acceptable salt or co-crystal thereof, in association with a pharmaceutically acceptable adjuvant, diluent or carrier.

11. A pharmaceutical composition comprising (i) a compound of claim 1, (ii) an additional therapeutic agent, or a pharmaceutically acceptable salt thereof, and (iii) one or more pharmaceutically acceptable excipient, carrier or diluent.

12. A pharmaceutical composition comprising (i) a compound of claim 1, together with a pharmaceutically acceptable excipient, carrier or diluent (ii) an additional therapeutic agent, or a pharmaceutically acceptable salt thereof, together with a second pharmaceutically acceptable excipient, carrier or diluent.

13. The pharmaceutical composition according to claim 11, wherein at least one agent is selected from the group consisting of methotrexate, sulfasalazine and hydroxychloroquine, or a pharmaceutically acceptable salt thereof.

14. The pharmaceutical composition according to claim 11, wherein at least one agent is selected from the group consisting of infliximab, adalimumab, certolizumab, etanercept, golimumab, tocilizumab, rituximab, abatacept, anakinra, secukinumab, ixekizumab or ustekinumab.

15. A process for the preparation of a compound of claim 1, the process comprising the steps of:
(i) mixing sulfasalazine and 1.0 to 1.5 equivalent of base in an organic solvent under stirring for 0.5 to 4 h at a temperature between 15 and 60° C.,
(ii) adding 1.0 to 1.5 equivalent of halo-acetamide in an organic solvent under stirring for 10 to 48 h at a temperature between 60 to 130° C., optionally in the presence of KI,
(iii) cooling and partition between an aqueous saturated NaCl solution and organic solvent, drying the organic solvent using an anhydrous $MgSO_4$ or $Na_2SO_4$ or similar, filtrating and evaporating the solvent, and
purifying using chromatography and/or crystallization.

16. A method of preventing, delaying progression or treating an autoimmune disease in a subject comprising administering to the subject a compound of claim 1.

17. A method of preventing, delaying progression or treating an arthritis in a subject comprising administering to the subject a compound of claim 1, wherein the arthritis is selected from rheumatoid arthritis and the active juvenile idiopathic form thereof, Stills' disease, oligoarthritis and the active juvenile idiopathic form thereof, polyarthritis and the active juvenile idiopathic form thereof, seronegative spondyloarthropathies including ankylosing spondylitis, spondyloarthropathy with peripheral arthritis, axial spondyloarthritis and the active juvenile idiopathic forms thereof.

18. A method of preventing, delaying the progression or treating an inflammatory bowel disease in a subject comprising administering to the subject a compound of claim 1.

19. The method of claim 18, wherein the inflammatory bowel disease is selected from eosinophilic gastro-enteritis, mastocytosis, Crohn's disease, colitis including ulcerative colitis, proctitis, coeliac disease, irritable bowel syndrome, and food-related allergies, which may have effects remote from the gut, such as migraine, rhinitis or eczema, including juvenile idiopathic forms thereof.

20. A method of modulating an autoinflammatory response in a subject comprising administering to the subject a composition of claim 10.

* * * * *